United States Patent
Bakhoum et al.

(10) Patent No.: US 11,623,006 B2
(45) Date of Patent: Apr. 11, 2023

(54) METHODS AND COMPOSITIONS FOR INCREASING SUSCEPTIBILITY TO RADIATION TREATMENT BY INHIBITING SUPPRESSION OF NUMERICAL CHROMOSOMAL INSTABILITY OF CANCER CELLS

(71) Applicants: MEMORIAL SLOAN KETTERING CANCER CENTER, New York, NY (US); THE TRUSTEES OF DARTMOUTH COLLEGE, Hanover, NH (US)

(72) Inventors: Samuel F. Bakhoum, New York, NY (US); Bassem I. Zaki, Hanover, NH (US); Duane A. Compton, Hanover, NH (US)

(73) Assignees: Memorial Sloan Kettering Cancer Center, New York, NY (US); The Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 16/818,966

(22) Filed: Mar. 13, 2020

(65) Prior Publication Data
US 2020/0282054 A1 Sep. 10, 2020

Related U.S. Application Data

(63) Continuation of application No. 15/544,811, filed as application No. PCT/US2016/014400 on Jan. 21, 2016, now abandoned.

(60) Provisional application No. 62/106,204, filed on Jan. 21, 2015.

(51) Int. Cl.
*A61K 41/00* (2020.01)
*A61N 5/10* (2006.01)

(52) U.S. Cl.
CPC ............ *A61K 41/0038* (2013.01); *A61N 5/10* (2013.01); *A61N 2005/1098* (2013.01)

(58) Field of Classification Search
None
See application file for complete search history.

(56) References Cited

U.S. PATENT DOCUMENTS

2006/0177828 A1* 8/2006 Armour ................... C12N 9/14
435/325

FOREIGN PATENT DOCUMENTS

WO WO-2009/036297 A1 3/2009
WO WO-2012/078703 A2 6/2012

OTHER PUBLICATIONS

Kaestner, Phillip; Bastians, Holger; "Mitotic Drug Targets" Journal of Cellular Biochemistry, 111, 258-265, 2010 (Year: 2010).*
Sanhaji, Mourad; et al; "Mitotic centromere-associated kinesin (MCAK): a potential cancer drug target" Oncotarget, 2, 935-947, 2011 (Year: 2011).*
Bakhoum et al., "Numerical chromosomal instability mediates susceptibility to radiation treatment," Nature Comm., vol. 6, No. 1 (Jan. 21, 2015).
Bassem et al., "Chromosomal instability portends superior response of rectal adenocarcinoma to chemoradiation therapy," Cancer, pp. 1733-1742 (Mar. 6, 2014).
Colombo, et al., Targeting the Mitotic Checkpoint for Cancer Therapy with NMS-P715, an Inhibitor of MPS1 Kinase. Cancer Research. 2010, pp. 10255-10264, No. 70.
Mo, et al., Inhibition of Hec1 expression enhances the sensitivity of human ovarian cancer cells to paclitaxel. Acta Pharmacologica Sinica. 2013, pp. 541-548, No. 34.
Morales, et al., BUB1 and BURB1 inhibition decreases proliferation and colony formation, and enhances radiation sensitivity in pediatric glioblastoma cells. Childs Nerv Syst. 2013, pp. 2241-2248, No. 29.
Tandle, et al., Abstract 1584: Targeting the mitotic checkpoint with inhibition of MPS1 kinase enhances radiosensitivity of glioblastoma cancer cells. Cancer Research. Apr. 2013, Abstract 1584, vol. 73, Issue 8, Washington DC.
Nagalaxmi et al., "A role of radioprotective agents in cancer therapeutics: a review," Int. Jour. of Basic and Clinical Pharmacology, vol. 2, No. 6, (Jan. 1, 2013).

* cited by examiner

*Primary Examiner* — David W Berke-Schlessel
(74) *Attorney, Agent, or Firm* — Foley & Lardner LLP

(57) ABSTRACT

Disclosed is a method for increasing susceptibility of cancer cells to ionizing radiation by delivering to the cells a radiosensitizing agent that has one of the following properties: it perturbs the process of chromosome segregation thereby increasing chromosome missegregation; or (b) it is an inhibitor of an agent that promotes faithful chromosome segregation induces numeric chromosome instability in said cells and this instability is induced substantially simultaneously with or closely prior to or closely after irradiating the cells. Examples of such radiosensitizing agent include inhibitors of one or more of the following: Kif2b, MCAK, MPS1, Eg5/Kinesin-5 5, Polo-like kinase 4, MCAK, Bub1 and Hec1. Such agents specifically target proteins involved in maintaining or promoting faithful chromosome segregation.

6 Claims, 14 Drawing Sheets

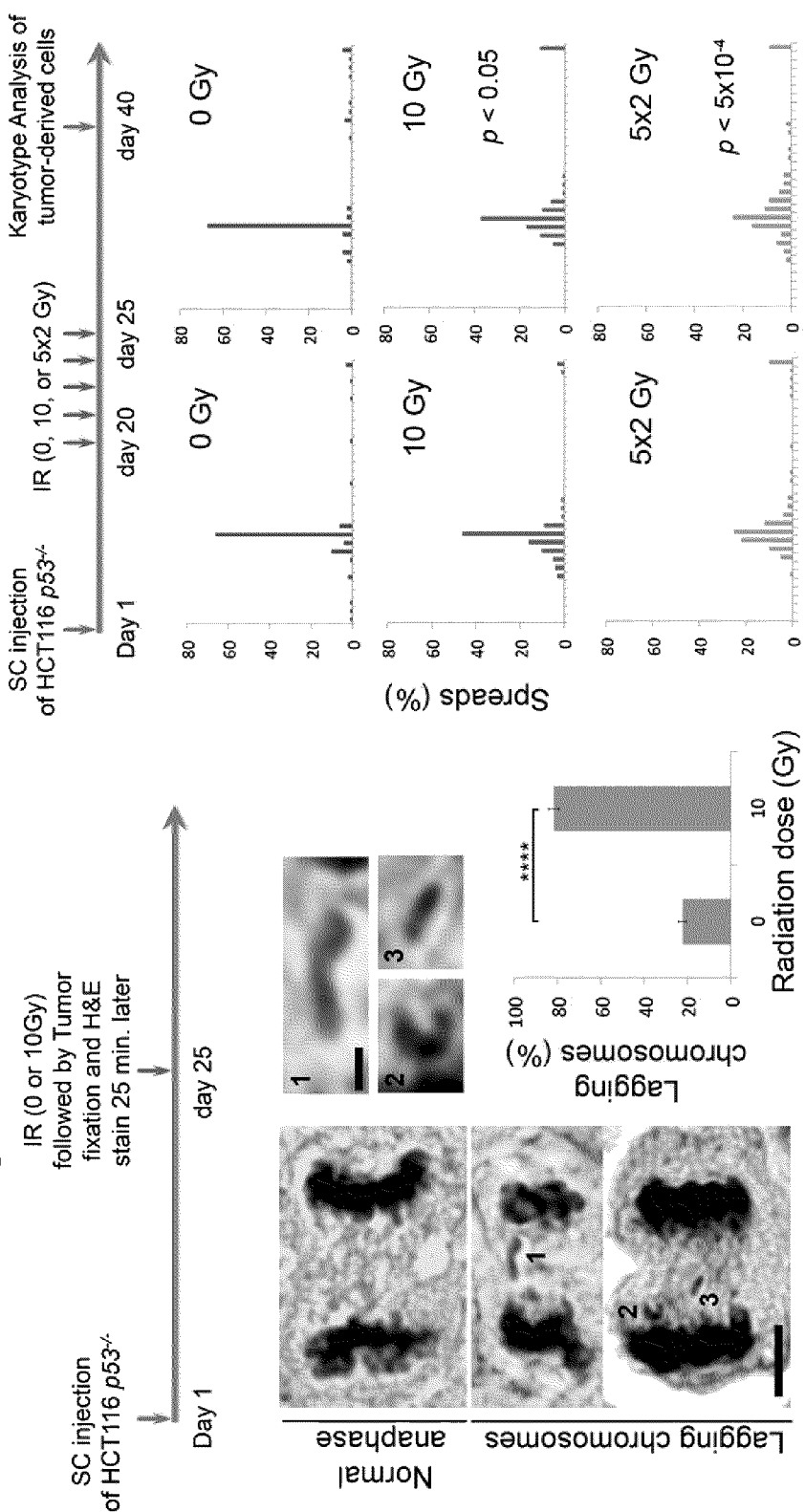

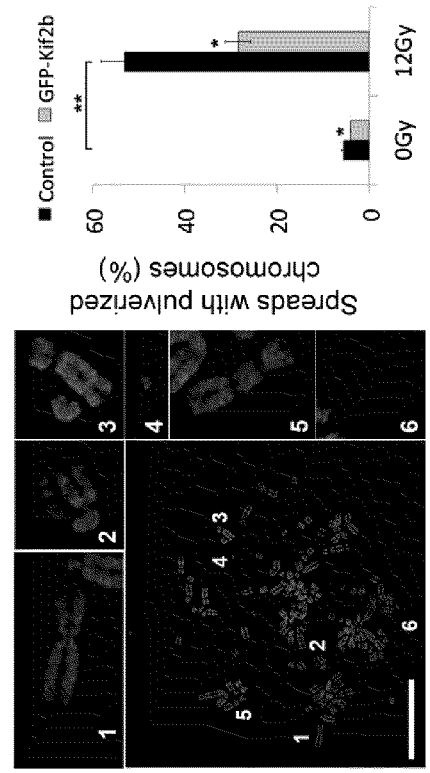
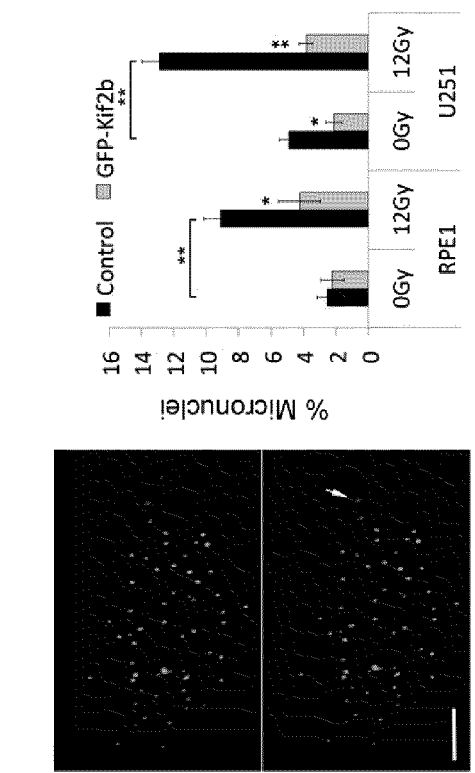

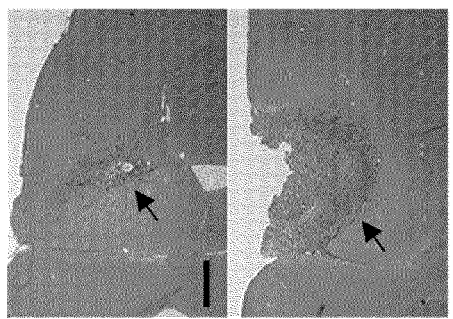
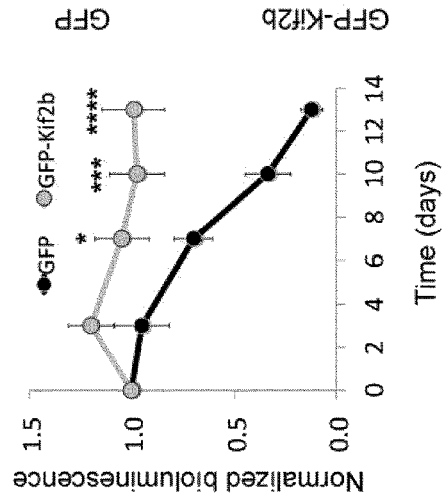
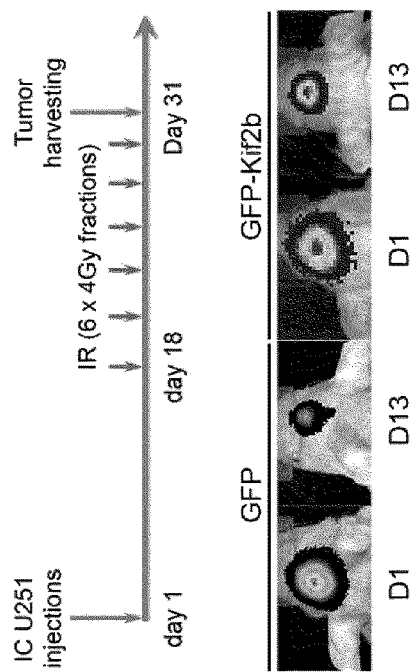
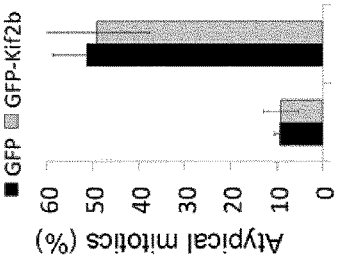
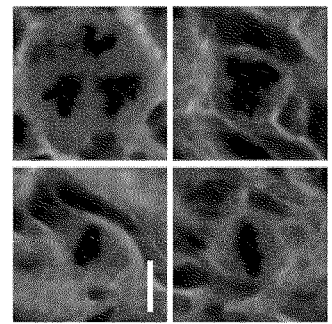
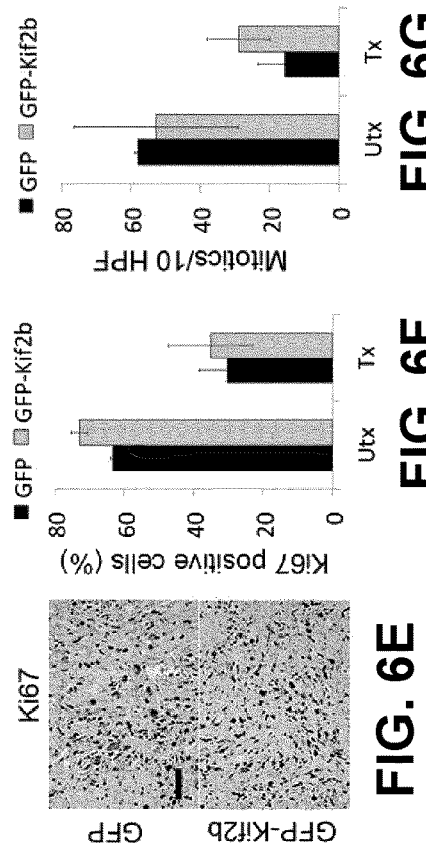

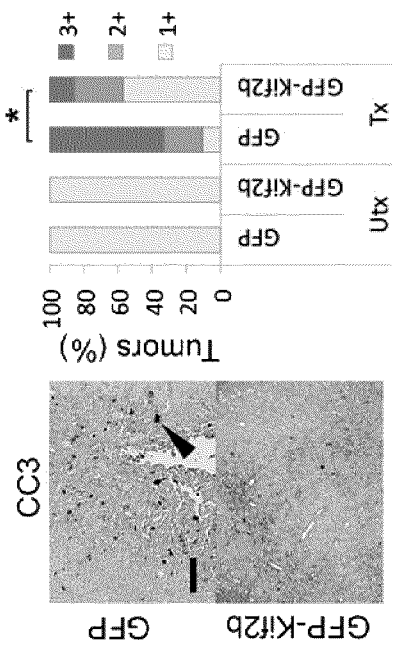
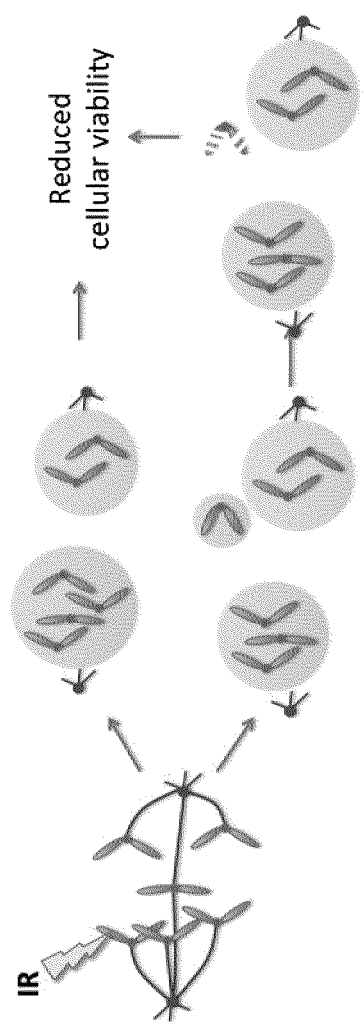

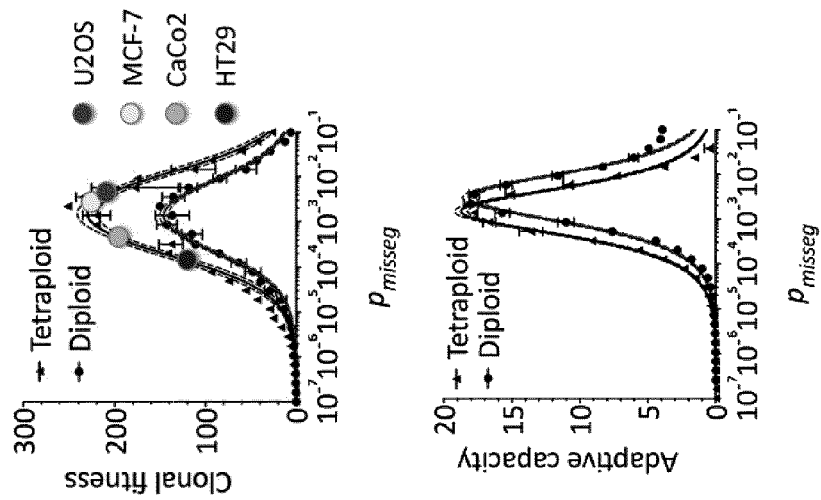
FIG. 11B
FIG. 11C
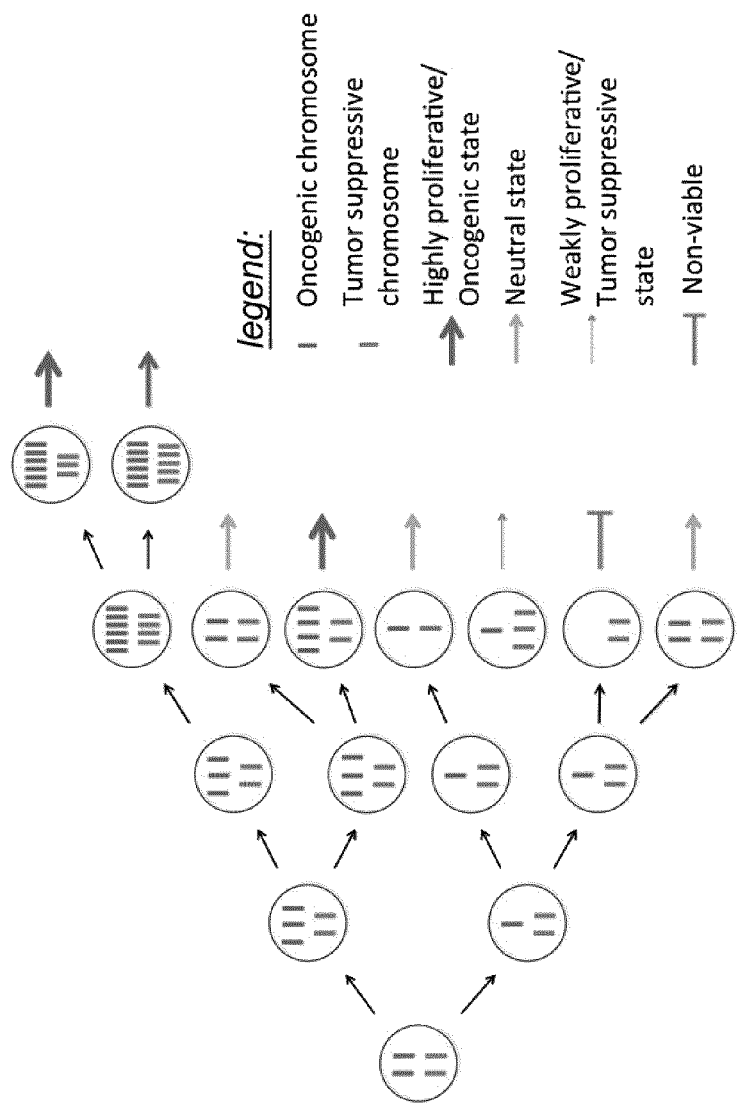
FIG. 11A

METHODS AND COMPOSITIONS FOR INCREASING SUSCEPTIBILITY TO RADIATION TREATMENT BY INHIBITING SUPPRESSION OF NUMERICAL CHROMOSOMAL INSTABILITY OF CANCER CELLS

CROSS-REFERENCE TO RELATED APPLICATIONS

This application is a continuation of U.S. patent application Ser. No. 15/544,811, filed Jul. 19, 2017, which is a National Stage Application of PCT/US2016/014400, filed Jan. 21, 2016, which claims priority to U.S. Provisional Patent Application No. 62/106,204, filed Jan. 21, 2015, the entire contents of each of which is incorporated herein by reference.

GOVERNMENT SUPPORT

This invention was made with government support under GM051542 awarded by the National Institutes of Health. The government has certain rights in the invention.

BACKGROUND OF THE DISCLOSURE

Technical Field

The present disclosure relates to the field of cancer therapy using agents that promote whole-chromosomal instability, as irradiation sensitization agents, and thus to make patients more sensitive to radiation therapy, thereby increasing the effect of radiation therapy.

Background and Description of Related Art

Radiation therapy is an integral modality in cancer treatment. The lethal effect of ionizing radiation (IR) lies in its ability to cause widespread genomic damage primarily in the form of DNA double-strand breaks (DSBs). Each Gray (Gy) of IR has been proposed to directly induce ~35 DNA DSBs per cell. This overwhelming damage generally overcomes the ability of tumor cells to repair DSBs, leading to a reduction in cellular viability and to cell death. DNA damage produced by IR can be repaired through homologous recombination (HR) and non-homologous end joining (NHEJ). HR repair is less error-prone than NHEJ, as the latter can join DSB ends of genomic DNA, which can lead to chromosomal translocations, acentric chromatin fragments as well as dicentric chromosomes which have two centromeres. Acentric chromatin fragments exhibit a high likelihood of missegregation during the subsequent mitosis, as they are incapable of establishing canonical attachment to spindle microtubules at the kinetochores. Alternatively, dicentric chromatin often leads to the formation of chromatin bridges where each centromere is attached to microtubules emanating from opposite spindle poles. Forces exerted by the mitotic spindle break chromatin bridges in a process termed the breakage-fusion-bridge cycle. This cycle can also be initiated by telomere dysfunction and replication stress. It is thus clear that DNA breaks generated by IR in dividing cells can directly lead to structural chromosomal instability (s-CIN), whose hallmarks are chromatin bridges and acentric chromatin fragments.

Another form of genome instability, present in the majority of solid tumors, is numerical (or whole) chromosomal instability (w-CIN). w-CIN primarily arises from errors in whole chromosome segregation during mitosis and it generates widespread aneuploidy in tumor cells. A phenotypic hallmark of w-CIN, both in cell culture and human tumor samples, is the presence of chromosomes that lag in the middle of the mitotic spindle during anaphase. These lagging chromosomes can directly lead to chromosome missegregation and aneuploidy. w-CIN does not exist separately from s-CIN, as it was recently shown that lagging chromosomes can also undergo severe structural damage by generating whole-chromosome containing micronuclei. These micronuclei are defective in DNA replication and repair and possess a faulty nuclear envelope leading to the pulverization of their enclosed chromosomes. Thus w-CIN can in turn lead to s-CIN.

Given the interrelatedness of w-CIN and s-CIN we asked whether IR could directly generate numerical chromosomal abnormalities. Experimental and clinical evidence suggest that, in addition to direct DNA breaks, IR can lead to changes in chromosome numbers. Furthermore, we recently demonstrated that activation of the DNA damage response pathway during mitosis, using IR or Doxorubicin, directly leads to the formation of lagging chromosomes during anaphase. This suggests that IR has the potential to generate both w-CIN and s-CIN in a context-dependent manner.

The sensitivity of cells to IR is not only dependent on the amount of DNA damage that immediately results from IR exposure; pre-existing damage or the inability to repair this damage are also important determinants of cellular viability. In the clinical setting, the relationship between s-CIN and IR has long been recognized, whereby genetically unstable tumors with intrinsically elevated rates of s-CIN or decreased DNA repair ability are more likely to respond to radiation treatment. Accordingly, many known chemotherapeutic agents that sensitize tumors to ionizing radiation act by either promoting DNA damage or impairing DNA repair. (It should be noted, however, that these chemotherapeutic agents are not targeted specifically to increasing whole chromosome instability.) On the other hand, the role of w-CIN in mediating sensitivity to IR is much less understood. This is particularly relevant given that mitosis has long been recognized as the most radiosensitive phase of the cell cycle, thus offering a potentially important therapeutic target. Along these lines, the present inventors and coworkers recently found that, in patients diagnosed with rectal adenocarcinoma, elevated pre-treatment rates of chromosome segregation errors forebode superior response to chemoradiation therapy. This inspired the present inventors to investigate whether pre-existing defects related to w-CIN that manifest as lagging chromosomes may also play a role in determining sensitivity to IR. Furthermore, the inventors asked whether w-CIN can be used to increase or decrease the sensitivity of a dividing cell to ionizing radiation.

SUMMARY OF THE DISCLOSURE

As described herein, the present disclosure provides new experimental evidence elucidating one of the mechanisms—previously unreported—by which cell-cycle dependent vulnerability of cancer cells undergoing mitosis to ionizing radiation occurs.

The inventors have shown that treatment with ionizing radiation leads to mitotic chromosome segregation errors in vivo and to long-lasting aneuploidy in tumor-derived cell lines. These mitotic errors generate an abundance of micronuclei that predispose chromosomes to subsequent catastrophic pulverization by IR thereby independently amplifying radiation-induced genome damage. Experimentally suppressing whole chromosome missegregation (which if not supported would lead to numerical or whole chromosome instability) reduces downstream chromosomal defects and significantly increases the viability of irradiated mitotic cells, giving rise to tumor cell resistance to further radiation. Further, orthotopically transplanted human glioblastoma tumors in which chromosome missegregation rates have been reduced through overexpression of kinesins are rendered markedly more resistant to ionizing radiation, exhibiting diminished markers of cell death in response to radiation treatment. This disclosure thus identifies a novel mitotic pathway for radiation-induced genome damage, which occurs outside the primary nucleus and augments chromosomal breaks. This relationship between radiation treatment and whole chromosome missegregation can be exploited to enhance efficacy of radiation treatments of solid malignant tumors susceptible to radiation treatment and thus to reduce the likelihood of resistance. It can also be used to spare noncancerous tissues or organs from deleterious effects of radiation.

Accordingly, in one aspect, the present disclosure provides a method for increasing susceptibility of cancer cells to ionizing radiation to a radiosensitizing agent that has one of the following properties: (a) it perturbs the process of chromosome segregation thereby increasing chromosome missegregation; or (b) it is an inhibitor of an agent that promotes faithful chromosome segregation induces numeric chromosome instability in said cells and this instability is induced substantially simultaneously with or closely prior to or closely after irradiating the cells.

In some embodiments the radiosensitizing agent inhibits one or more of the following directly or indirectly: Kif2b, MCAK, MPS1, Eg5/Kinesin-5, Polo-like kinase 4, MCAK, Bub1 and Hec1. The agent thus specifically targets proteins involved in maintaining or promoting faithful chromosome segregation.

In some embodiments, the cancer cells are solid tumor cancer cells for which radiation is an indicated therapeutic modality. Nonlimiting examples of such tumors include head-and-neck cancer, rectal adenocarcinoma, glioblastoma multiform.

In some embodiments, the radiosensitizing agent is selected from the group consisting of MPS1 inhibitors, Eg5/Kinesin-5 inhibitors, Polo-like kinase 4 inhibitors, MCAK inhibitors, Bub1 inhibitors and Hec1 inhibitors. (Bub1 and Hec1 inhibitors will produce the desired chromosomal instability but so will activators as described below.)

The ionizing radiation is administered in one or in multiple (at least two) divided doses.

In another aspect, the present disclosure provides a method for increasing cytotoxicity of ionizing radiation in a subject to be treated for a solid malignant tumor susceptible to treatment with ionizing radiation, the method comprising administering systemically to the subject or locally to the tumor an inhibitor of suppression of numerical chromosome instability incident to a first dose of said radiation, thereby enhancing chromosome missegregation during mitosis substantially simultaneously with or closely preceding treatment of the tumor with a subsequent dose of ionizing radiation. This subsequent dose can be delivered either closely before, closely after or up to 1 or even 2 months after increasing chromosomal instability as long as the chromosomal instability induction substantially persists.

A method is also provided for reducing damage of noncancerous cells or tissue incident to ionizing radiation aimed at cancerous cells or tissue comprising exposing the noncancerous cells or tissue to a radioprotective agent (such as agonists of Kif2b or MCAK) which is an enhancer of suppression of chromosome missegregation and reduces numeric chromosome instability in said cells simultaneously with or immediately prior to or immediately following irradiating the cancerous cells or tissue with a therapeutically effective dose and regimen of ionizing radiation.

The radioprotective agent is or specifically activates a protein involved in faithful chromosome segregation maintenance.

In some embodiments, the radioprotective agent is Kif2b or MCAK or an agonist or activator of Kif2b or MCAK.

A clarifying detail is that presence of initial chromosome instability in a cell makes the cell more susceptible to induction of further chromosome instability by the methods recited above; conversely, presence of initial chromosome stability in a cell makes a cell more likely to respond to a radioprotective agent. Thus, in accordance with the present methods, w-CIN in induced preferentially in cancer cells. Main contributors to cancer cell specificity are the following: 1) induction of w-CIN according to the present disclosure occurs mostly in rapidly dividing cells (such as cancer cells); and 2) the higher chromosomal missegregation before treatment, the more sensitive cells are to interventions aimed at further increasing w-CIN.

In some embodiments, the tumor includes, but is not limited to tumors of the following organs: the skin, breast, brain, cervix, testis, heart, lung, gastrointestinal tract, genitourinary tract, liver, bone, nervous system, reproductive system, and adrenal glands. In more detail, adrenal tumors include for example adrenocortical carcinoma, bile duct, bladder, bone (e.g., Ewing's sarcoma, osteosarcoma, malignant fibrous histiocytoma), brain/CNS (e.g., astrocytoma, glioma, glioblastoma, childhood tumors, such as atypical teratoid/rhabdoid tumor, germ cell tumor, embryonal tumor, ependymoma), breast (including without limitation ductal carcinoma in situ, carcinoma, cervical, colon/rectum, endometrial, esophageal, eye (e.g., melanoma, retinoblastoma), gallbladder, gastrointestinal, kidney (e.g., renal cell, Wilms' tumor), heart, head and neck, laryngeal and hypopharyngeal, liver, lung, oral (e.g., lip, mouth, salivary gland) mesothelioma, nasopharyngeal, neuroblastoma, ovarian, pancreatic, peritoneal, pituitary, prostate, retinoblastoma, rhabdomyosarcoma, salivary gland, sarcoma (e.g., Kaposi's sarcoma), skin (e.g., squamous cell carcinoma, basal cell carcinoma, melanoma), small intestine, stomach, soft tissue sarcoma (such as fibrosarcoma), rhabdomyosarcoma, testicular, thymus, thyroid, parathyroid, uterine (including without limitation endometrial, fallopian tube), and vaginal tumor and the metastasis thereof. In some embodiments, the tumor is selected from the group consisting of breast, lung, GI tract, skin, and soft tissue tumors. In some further embodiments the tumor is selected from the group consisting of breast, lung, GI tract and prostate tumors.

The present inventors thus have discovered that increasing chromosome missegregation together with radiation treatment would lead to sensitization of the tumor to radiation therapy. This in turn permits 1) to decrease dose of radiation and achieve the same effect, 2) to maintain dose of radiation and increase tumor sensitization in otherwise resistant tumors, 3) to increase radioprotection of normal organs.

BRIEF DESCRIPTION OF THE FIGURES

FIG. 1A are examples of U251 cells fixed 25 min after exposure to 12 Gy and exhibiting lagging chromosomes (LC), chromatin bridges (CB), acentric chromatin (AC) or a combination (LC+AC) obtained through high-resolution fluorescence microscopy. Scale bar, 5 µm. FIG. 1B is a series of bar graphs showing percentage of chromosome missegregation in anaphase spindles of RPE1, HCT116 and U251 cells as a function of IR dose. Bars represents mean±s.e.m., n=150 cells, three experiments, *P<0.01, two-tailed t-test. FIG. 1C are images obtained by FISH showing HCT116 nuclei stained for DNA (grey cloud right panel), centromere (white dots right panel) and telomere (white dots on the outer edges of grey cloud right panel) probes for human chromosome 2. White arrow denotes an aneuploid nucleus containing three copies of chromosome 2. Scale bar, 10 µm. FIG. 1D is a bar graph showing percent HCT116 nuclei containing whole-chromosome and segmental aneuploidy for chromosome 2. n=300 cells, *P<0.05. FIG. 1E is a bar graph showing percentage of chromosome missegregation in anaphase spindles of HCT116 p53$^{-/-}$ cells exposed to 0 Gy (top) or 6 Gy (bottom) as a function of time after irradiation (mo, months)

FIGS. 2A-2E show in vivo induction of chromosome segregation errors by IR. FIGS. 2A and 2D are schematic representations of experimental design. FIG. 2B is an image of H&E staining of SC-HCT116 p53$^{-/-}$ xenografts. FIG. 2C is a graph showing percentage of anaphase cells exhibiting lagging chromosome in response to IR. FIG. 2E is a graph of tumor-derived cells karyotype analysis.

FIGS. 3A-3C show that IR-induced chromosome segregation errors lead to widespread chromosomal damage. FIGS. 3A and 3D are schematic representations of experimental design. FIG. 3B is an image of cells containing micronucleus. FIG. 3C is a graph depicting percentage of cells containing micronuclei as a function of IR dose. FIG. 3E is an image of mitotic spread containing pulverized chromosomes. FIG. 3F is a graph showing percentage of mitotic spreads.

FIG. 4A is a graph showing fluorescence intensity of γ-H2AX in Kif2b overexpression cells. FIG. 4B is a graph showing the average number of γ-H2AX foci per nucleus as a function of IR dose in Kif2b overexpression cells. FIG. 4C is a series of images of cells stained for DNA and γ-H2AX following IR.

FIGS. 5A and 5B are graphs of surviving fraction of cells versus radiation dose.

FIGS. 6A-6L show that reducing chromosome segregation errors induces radiation resistance in vivo. FIG. 6A is a schematic representation of experimental design. FIG. 6B are bioluminescence images of mice. FIG. 6C is a graph showing normalized bioluminescence over time in xenografts. FIG. 6D is an image showing H&E staining. FIG. 6E is an image showing Ki67 positive cells. FIG. 6F is a graph showing percentage of Ki67 positive cells. FIG. 6G is a graph showing mitotic count in U251 xenografts. FIG. 6H is an image of atypical mitotic cells. FIG. 6I is a graph showing a percent of atypical mitotic cells in xenografts. FIG. 6J is an image showing cleaved caspase 3 (CC3) tumor. FIG. 6K is a graph showing quantification of CC3 positive cells. FIG. 6L is a schematic representation linking IR to chromosome segregation errors and downstream chromosomal structural defects.

FIGS. 7A and 7B are images of anaphase spindle in U251 cells. FIG. 7C is an autoradiograph of a Western blot of U251 cells stained with GFP and DM1-α antibodies.

FIG. 8A is a plot of surviving cellular fraction and radiation dose. FIG. 8B is a plot of number of cells per plate as a function of time. FIG. 8C is a bar graph showing karyotypic distribution of GFP-expressing and GFP-Kif2b expressing U251 cells.

FIGS. 11A-11C show computational models of w-CIN in clonally expanding populations. FIG. 11A is a schematic of cancer cells, which frequently missegregate whole chromosomes leading to karyotypic heterogeneity. FIGS. 11B and 11C are distribution curves showing respectively the dependence of clonal fitness (FIG. 11B) and adaptive capacity (FIG. 11C) on chromosome missegregation rates (pmisseg) for diploid and tetraploid-derived clonal populations.

DETAILED DESCRIPTION

Figure 1A:
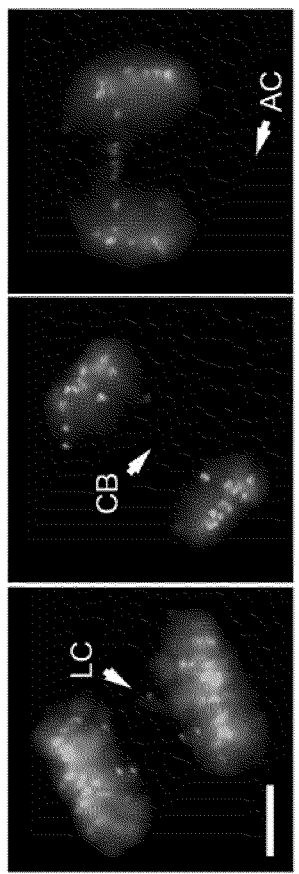
FIGS. 1A-1E are a combination of high-resolution immunofluorescence microscopy images and graphical representation thereof showing that w-CIN is induced by IR in vitro.

The present disclosure is based on the following discoveries:

Definitions

As used herein, the following terms and abbreviations shall have the meaning ascribed to them below unless the context clearly indicates otherwise.

"Subject" means a patient (human or veterinary) or an experimental animal, such as a mouse or other rodent.

"Time interval of increased susceptibility" means the period of time after administration of the CIN promoting agent, or radiosensitizing agent during which the resulting increase in w-CIN or lagging chromosomes is still substantially present.

"Effective amount" is an amount of a radiosensitizing agent or a radioprotective agent according to the present disclosure sufficient to increase or to decrease w-CIn by at least 5%. This amount varies greatly from agent to agent and may also vary widely (from picograms to milligrams perkilogram of patient weight) according to the tumor and the age and physical condition of the patient as well as other factors. Examples and guidance of effective amounts are provided in the discussion of particular agents.

The term "ionizing radiation" means any radiation where a nuclear particle has sufficient energy to remove an electron or proton or other particle from an atom or molecule, thus producing an ion and a free electron or radical. Examples of such ionizing radiation include, but are not limited to, gamma rays, X-rays, protons, electrons, alpha particles, carbon atoms, or particles emitted from a radioactive source including, but not limited to, yttrium and radium. Radiation from implanted material is included. Ionizing radiation is commonly used in medical radiotherapy and the specific techniques for such treatment will be apparent to a person of ordinary skill in the art. Other examples of radiation suitable for use in the present methods are provided elsewhere in the specification.

The term "radiosensitizing agent" means agents which increase the susceptibility of cells to the damaging effects of ionizing radiation or which become more toxic to a cell after exposure of the cell to ionizing radiation. A radiosensitizing agent may permit lower doses of radiation to be administered and still provide a therapeutically effective dose. In the context of the present disclosure, agents that increase chromosome missegregation by specifically targeting proteins that are involved in chromosome missegregation (activating such proteins) or in faithful chromosome segregation (inhibiting such proteins) are radiosensitizing agents. Conversely, those agents that suppress (or more accurately increase the suppression of) chromosome missegregation can be referred to as "radioprotective agents." The latter have the property of enhancing suppression of chromosomal missegregation and reducing numeric chromosomal instability.

"Closely" in the context of timing of administration means during an interval of increased radiosensitization of a cancerous cell (while the induced w-CIN substantially persists). This interval can be as short as about 1 hour to about 8 hours, but may extend to about 24 hours, or up to about 1 month or even 2 prior to an irradiation dose depending on the duration of induced w-CIN.

"Substantially" in the context of a measurable property means "mostly," or "a major portion of" (for example 50% or more). Thus a cell substantially retaining induced w-CIN means retaining at least about half of the induced increase in w-CIN perpetrated by a radiosensitizing agent. CIN is considered increased by reference to an untreated cell id it is at least 5% higher than the chromosomal instability of an untreated cell. "Substantially" in the context of "substantially simultaneously" mean at the same time or almost at the same time, e.g., within the same day or 24-hour period.

"Tumor" as used herein means primary or metastatic tumor and includes the list of the tumor in the summary, above.

Radiation Therapy

The present disclosure provides for sensitization of tumours to radiation therapy, where radiation therapy can include any radiation used in cancer treatment. The radiation may be curative, adjuvant, or palliative radiotherapy. Such radiation includes, but is not limited to, various forms of ionizing radiation (e.g., as listed supra), external beam radiotherapy (EBRT or XBRT) or teletherapy, brachytherapy or sealed source therapy, radioactive implant therapy, intraoperative radiotherapy, and unsealed source radiotherapy.

In some embodiments, the radiation is ionizing radiation. Radiation may be electromagnetic or particulate in nature. Electromagnetic radiation includes, but is not limited to, x-rays and gamma rays. Particulate radiation includes, but is not limited to, electron beams, proton beans, neutron beams, alpha particles, and negative pimesons. The unit of absorbed dose is the gray (Gy), which is defined as the absorption of 1 joule per kilogram. As is appreciated by those of skill in the art, the energy of the radiation determines the depth of absorption as well as the nature of the atomic interaction. Radiotherapy can be administered by a conventional radiological treatment apparatus and methods, or by intraoperative and sterotactic methods. Radiation may also be delivered by other methods that include, but are not limited to, targeted delivery, systemic delivery of targeted radioactive conjugates and intracavitary techniques (brachytherapy). Other radiation methods not described above can also be used to practice this invention.

In accordance with the present disclosure, ionizing radiation is used to target tissues or cells, such as neoplastic tissues or cells, for selective delivery of an CIN promoting active agent via a delivery vehicle comprising the active agent. Thus, the target tissues or cells are exposed to ionizing radiation, and a delivery vehicle comprising the active CIN promoting agent is administered before, during, or both before and during the exposure to radiation. Radiation immediately preceding delivery of the CIN promoting agent to the tumor is also possible or even 2.

In one embodiment, radiation therapy is delivered using radioactive isotopes (brachytherapy). This can be either high-dose rate or low dose rate brachytherapy. High dose rate brachytherapy is usually delivered using Ir-192 (but not exclusively) and can be given in one or more doses and doses. Low dose rate brachytherapy can be delivered using radioactive palladium or iodine and it involves permanent or long-term placement of seeds in and around the target and dose delivery obeys the half-life of the decay of the radioactive substance and can take weeks to months to deliver the majority of the dose.

In particular embodiments, the methods described herein can be used in the treatment of various types of solid tumors. Examples of solid tumors have been provided in the Summary of the Disclosure.

In more detail, malignant tumors which can be treated by methods described herein can be used in the treatment of cancer, include without limitation adrenal tumors (e.g., adrenocortical carcinoma), anal, bile duct, bladder, bone tumors (e.g., Ewing's sarcoma, osteosarcoma, malignant fibrous histiocytoma), brain/CNS (tumors e.g., astrocytoma, glioma, glioblastoma, childhood tumors, such as atypical teratoid/rhabdoid tumor, germ cell tumor, embryonal tumor, ependymoma), breast tumors (including without limitation ductal carcinoma in situ, carcinoma, cervical, colon/rectum, endometrial, esophageal, eye (e.g., melanoma, retinoblastoma), gallbladder, gastrointestinal, kidney (e.g., renal cell, Wilms' tumor), heart, head and neck, laryngeal and hypopharyngeal, liver, lung, oral (e.g., lip, mouth, salivary gland) mesothelioma, nasopharyngeal, neuroblastoma, ovarian, pancreatic, peritoneal, pituitary, prostate, retinoblastoma, rhabdomyosarcoma, salivary gland, sarcoma (e.g., Kaposi's sarcoma), skin (e.g., squamous cell carcinoma, basal cell carcinoma, melanoma), small intestine, stomach, soft tissue sarcoma (such as fibrosarcoma), rhabdomyosarcoma, testicular, thymus, thyroid, parathyroid, uterine (including without limitation endometrial, fallopian tube), and vaginal tumor and the metastases thereof. In some embodiments, the tumor is selected from the group consisting of breast, lung, GI tract, skin, and soft tissue tumors.

Radiation Dosage and Administration Regimen

Administration of radiation can be made by any appropriate means known to those of ordinary skill in the art. Radiation can be suitably administered in a dose effective for the particular cancer to be treated, as determined by a person of ordinary skill in the art. The dose of radiation used in conjunction with the agents that specifically promote w-CIN may be similar to the amount administered when radiation is used alone, or, may be reduced. In some instances, the dosage of radiation may be determined in relation to tumor volume and may depend on the type of tumor being treated. The dosage may also take into account other factors that can be determined by an ordinarily skilled clinician.

Radiation treatment may be given as fractionated doses or as a bolus dose. For example, radiation can be administered in a range of 1 to about 50 fractions, with each fraction size being within the range of 0.1 to about 50 Gy. In some embodiments, dosage of each fraction is about 2 to about 30 Gy. In other embodiments, dosage of each fraction is about 4 to about 25 Gy. In yet other embodiments, dosage of each fraction is about 10 to about 20 Gy. Particular dosage amounts include, but are not limited to, 0.4 (or 40 cGY), 1, 2, 4, 10 and 20 Gy.

In some embodiments, the source of ionizing radiation comprises an external beam photon irradiation source, which is typically utilized at energy levels ranging from about 10 kV (KeV) to about 18 MV (MeV) per photon beam, or a brachytherapy source directly applied in the tumor cavity. These sources of radiation can include, but are not limited to, yttrium, radium. In some embodiments, the source of ionizing radiation comprises an external beam electron irradiation source, which is typically utilized at energy levels ranging from about 10 KeV to about 20 MeV per electron beam. In some embodiments, the source of ionizing radiation comprises an external beam proton irradiation source, which is typically utilized at energy levels ranging from about 10 MEV to about 300 MeV per proton beam.

In the case of external beam radiation therapy, appropriate blocks, wedges, and boluses are used to deliver adequate dose to the planned target volume of target tissue. A preferred minimum source-axis distance comprises about 80 cm but can range considerably up and down as those skilled in the art appreciate. The subject receives local-regional irradiation via fields that are designed to encompass sites of disease requiring palliation or primary treatment while endeavoring to spare noncancerous tissue as much as possible.

Study, site, treatment intent and normal tissue considerations are also evaluated in the determination of dose. Examples of preferred dosages ranges are as follows. For an ionizing radiation dose that is administered in 1 fraction, a preferred dosage range comprises about 500 to about 1500 cGy, and at times 2400 cGy, with a preferred dosage range comprising about 800 to about 1200 cGy. For an ionizing radiation dose that is administered in 5 fractions, a preferred dosage range comprises about 1000 to about 3000 cGy, and at times up to 800 cGy, with a preferred dosage range comprising about 1500 to about 2500 cGy, and with a more preferred dosage amount comprising about 200 cGy. For an ionizing radiation dose that is administered in 10 fractions, a preferred dosage range comprises about 1000 to about 6000 cGy, with a preferred dosage range comprising about 2000 to about 4000 cGy, and with a more preferred dosage amount comprising about 3000 cGy.

For an ionizing radiation dose that is administered in 15 fractions, a preferred dosage range comprises about 1000 to about 7000 cGy, with a preferred dosage range comprising about 2000 to about 5000 cGy, and with a more preferred dosage amount comprising about 3500 CGy. For an ionizing radiation dose that is administered in 30 fractions, a preferred dosage range comprises about 2000 to about 12000 cGy, with a preferred dosage range comprising about 4000 to about 8000 cGy, and with a more preferred dosage amount comprising about 6000 cGy.

In some embodiments, radiation is administered 1 to about 50 times. Frequency of radiation treatment can be from 3 times per day to about once per month. In further embodiments, radiation is administered once per 3 weeks, once per 2 weeks, once per week, 2-6 times per week, at least once a day, twice a day or three times a day, or any combination thereof. For example, a suitable administration regimen includes a schedule where fractionations are given 2 times per day for 2 days followed by a month long pause, and this cycle is repeated numerous times.

Treatment can be administered for 2-8 consecutive or non-consecutive weeks. Whether given as a bolus or as fractionated doses, total dose of radiation may be, for example, about 2-200 Gy in 2 Gy fractions or an equivalent biological dose using other fractionation schemes. These are just examples of radiation treatment protocols, and the present disclosure encompasses other treatment protocols that may be determined by a clinician of ordinary skill in the art.

Actual dosage levels of the agent that promotes CIN and radiation may be varied so as to obtain the desired therapeutic response for a particular subject, composition and mode of administration, without being toxic to the subject. The selected dosage level will depend upon a variety of factors, including the route of administration, the rate of breakdown of the active form of the CIN promoting agent, the duration of treatment, other drugs, compounds, and/or materials used in combination with the particular CIN promoting agent, the age, sex, weight, condition, general health and prior medical history of the patient being treated, and similar relevant factors well known in the art.

When used as disclosed in the present disclosure, ionizing radiation may be used in the same amount and administration regimen. However, it may be possible through the use of radiosensitizing (and conversely radioprotective) agents to lower the dose or the frequency of administration, or both. Conversely, it may be possible to increase the same if used in combination with radioprotective agents. As stated above, methods for fine tuning the radiation intensity and frequency of administration are known in the art.

In one embodiment, high dose rate brachytherapy is given in one or more doses, where doses can range anywhere from about 0.1 Gy to about 50 Gy. In another embodiment, high dose rate brachytherapy is administered intra-operatively. In yet another embodiment, low dose rate brachytherapy is delivered using radioactive palladium or iodine and it involves permanent or long-term placement of seeds in and around the target and dose delivery obeys the half-life of the decay of the radioactive substance and can take weeks to months to deliver the majority of the dose. Furthermore, it is estimated that dose is delivered at a rate of anywhere between 0.001Gy-1Gy/hour in low-dose rate brachytherapy The therapeutic combination of the present disclosure can be combined with other cancer therapies, including, but not limited to, adjunct therapies (such as, but not limited to, surgical tumor resection and chemotherapy). Resection is often a standard procedure for the treatment of tumours. The types of surgery that may be used in combination with the present invention include, but are not limited to, preventative, curative and palliative surgery, and any other method that would be contemplated by those of skill in the art.

Agents that Promote/Induce Numeric Chromosome Instability

The agents in the categories described below all alter chromosome missegragation and eventually cause w-CIN by either specifically inhibiting Kif2b, MCAK, MPS1, Eg5/Kinesin-5, Polo-like kinase 4, Mad2, Hec1, Bub1, or BubR1 or by activating Mad2, Hec1, BubR1, or Bub1.

Inhibition of Kif2b and MCAK as Means of Inducing w-CIN

Figures 3G, 3H, 3I:
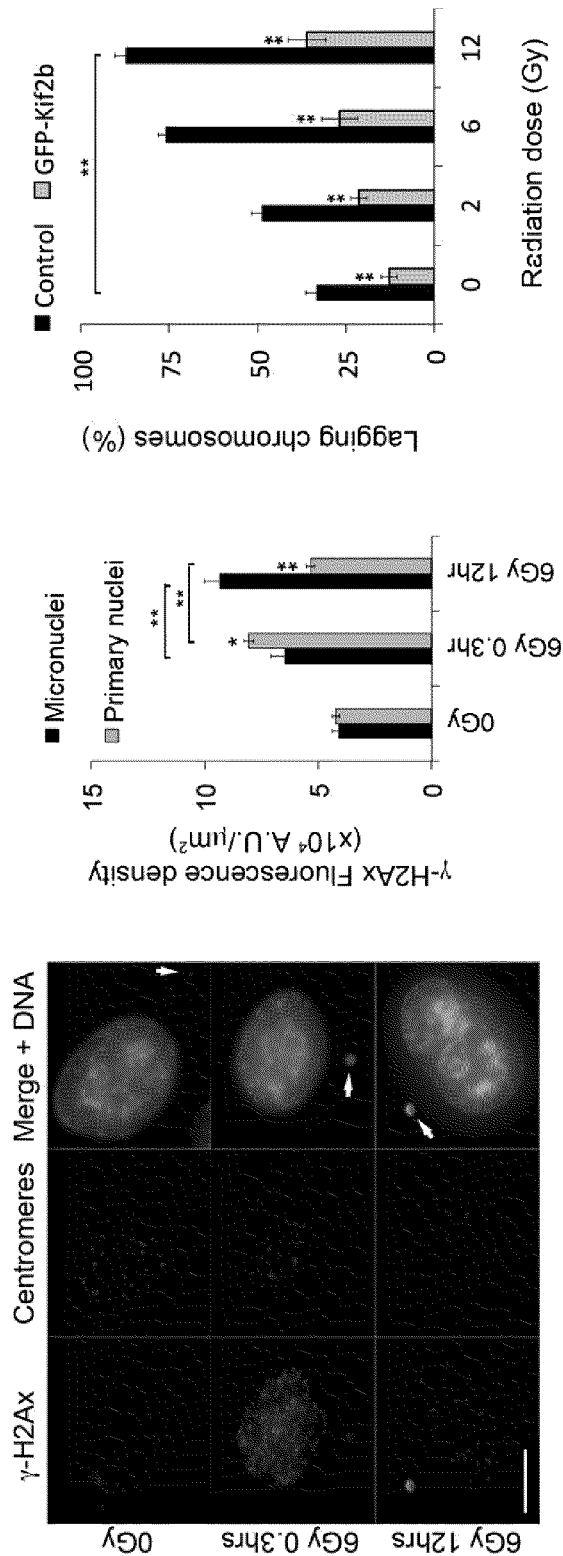
FIG. 3G is an image of cells containing micronuclei.
FIG. 3H is a graph of γ-H2AX fluorescence intensity following IR.
FIG. 3I is a graph showing a percentage of anaphase spindles containing lagging chromosomes as a function of IR dose.

The present disclosure provides evidence that over-expression of the microtubule-depolymerizing kinesin-13 proteins, Kif2b or MCAK, which localize to the attachment sites of chromosomes to spindle microtubules at the kinetochores, leads to the suppression of w-CIN in otherwise chromosomally unstable cell This suppression is persistent, lasting more than 30 days both in vitro and in vivo studies. Furthermore, Kif2b overexpressing cells displayed greater than twofold reduction in chromosome segregation errors during anaphase, which led to radiation resistance in vivo (FIG. 3I). These findings indicate that the inhibition of proteins that localize to the attachment sites of chromosomes to spindle microtubules at the kinetochores can be used to increase w-CIN in cancer cells and as such promote radiosensitization.

In one embodiment, suitable agents that induce numeric chromosomal instability are those that inhibit proteins that localize to the attachment sites of chromosomes to spindle microtubules at the kinetochores during mitosis. Proteins known to localize to the attachment sites of chromosomes to spindle microtubules at the kinetochores during mitosis include, but are not limited to Kif2b and MCAK. Thus, in one embodiment, suitable agents that induce numeric chromosomal instability are those that specifically target and inhibit Kif2b or MCAK.

Kif2b belongs to the kinesin-13 family of proteins and localizes to kinetochores during early mitosis (Manning A L. et al. Mol. Biol. Cell. 18:2970-2979 (2007)). For example, Kif2b can be inhibited using agents that inhibit Kif2b specifically. One such agent is DHTP ((Z)-2-(4-((5-(4-chlorophenyl)-6-(isopropoxycarbonyl)-7-methyl-3-oxo-3,5-dihydro-2H-thiazolo[3,2-a]pyrimidin-2-ylidene)methyl)phenoxy)acetic acid). DHTP has been shown to be a potent compound that inhibits kinein-13 induced microtubule depolymerization, where the $IC_{50}$ of DHTP in inhibiting Kif2b is 1.2 µM (FEBS Lett. 27; 588(14):2315-20 (2014)). In addition to Kif2b, DHTP possesses inhibitory activity against MCAK, with the $IC_{50}$ of DHTP in inhibiting MCAK is 4.6 µM FEBS Lett. 27; 588(14):2315-20 (2014)).

Additionally, Kif2b can be inhibited using agents that inhibit Kif2b specifically but indirectly (e.g., through specific activation or inhibition of another protein that inhibits or activates Kif2b). The possibility of such indirect specific effect is not limited to Kif2b but in principle extends to any radiosensitizing or radioprotective agent employed in the present methods.

Additional examples of MCAK inhibitors include MCAKsv1. See US Patent Application US20060177828 (Alternatively spliced isoform of mitotic centromere-associated kinesin (MCAK), Armour, Christopher, et al.; Filing Date Sep. 16, 2004; Publication Date Aug. 10, 2006).

Inhibition of MPS1 as Means of Inducing CIN

The core SAC kinases monopolar spindle-1 (Mps1, also known as TTK) is a serine threonine kinase which functions as a core component of the spindle assembly checkpoint (SAC) (Lauze' et al. EMBO J. 14, 1655-1663, (1995)), a key surveillance mechanism that monitors the attachment of spindle microtubules to the kinetochores of the chromosomes during pro-metaphase and halts the transitions to anaphase until all chromosomes are bi-oriented, fully attached, and correctly tensed at the metaphase plate. Mps1 is expressed in the mitosis phase of the cell cycle in proliferating cells. Mps1 activity causes cells to prematurely exit mitosis with unattached chromosomes, resulting in severe chromosome missegregation and aneuploidy (Colombo et al. Cancer Res., 70, 10255-10264 (2010); Jemaa et al. Cell Death Differ. 20, 1532-1545 (2013)). Overexpression of Mps1 has been observed in several cancer cell lines and tumor types including lung and breast cancers, where higher Mps1 levels correlate with worse prognosis.

Established anti-mitotic drugs such as vinca alkaloids, taxanes, or epothilones activate SAC either by destabilizing or stabilizing spindle microtubules resulting in mitotic arrest. Prolonged arrest in mitosis forces a cell either into a mitotic exit without cytokinesis or into a mitotic catastrophe leading to cell death. Such drugs do not target chromosome missegregation or faithful segregation specifically and are not included within the specifically acting agents of the present disclosure. In contrast to anti-mitotic drugs, specific Mps1 inhibitors inactivate the SAC and accelerate progression of cells through mitosis eventually resulting in severe chromosomal missegregation, mitotic catastrophe, and cell death. Consequently, Mps1 inhibition leads to failure of cells to arrest in mitosis in response to anti-mitotic drugs. Thus, the combination of microtubule-interfering agents and Mps1 inhibition strongly increases chromosomal segregation errors and cell death and therefore, constitutes an efficient strategy for selectively eliminating tumor cells.

Known Mps1 inhibitors include, but are not limited to BAY 1161909 (Bayer, Mps1 $IC_{50}$=1.9 nM, currently in Phase I (ClinicalTrials.gov ID: NCT02138812 (An Open-label Phase I Dose-escalation Study to Characterize the Safety, Tolerability, Pharmacokinetics, and Maximum Tolerated Dose of Oral BAY1161909 in Combination With Weekly Intravenous Paclitaxel Given in an Intermittent Dosing Schedule in Subjects With Advanced Malignancies), Mason et al. Cancer Cell, 26, 163-176, (2014)), BAY 1217389 (Bayer, Mps1 $IC_{50}$=1.1 nM, currently in Phase I (ClinicalTrials.gov ID: NCT02366949 (Phase I Study of Oral BAY 1217389 in Combination With Intravenous Paclitaxel)), S81694 (Nerviano Medical Sciences, Mps1 $IC_{50}$=3 nM, currently in pre-clinical development, (Colombo et al. Cancer Res., 70, 10255-10264 (2010)), and CFI-402257 (University Health Network, tdc.uhnresearch.ca/opportunities/small-molecule-tyrosine-threonine-ttkmps1-inhibitor/). BAY 1161909 has been administered orally, with a starting dose of 0.75 mg twice daily, on a 14-day cycle—D1, D2, D8, D9 and 28 day cycle—D8, D9 D15 and D16 of a 28 day cycle.

Other non-limiting examples of specific Mps1 inhibitors include N-(4-{2-[(2-cyanophenyl)amino][1,2,4]triazolo[1,5-a]pyridin-6-yl}phenyl)-2-phenylacetamide (Mps-BAY1) (a triazolopyridine), N-cyclopropyl-4-{8-[(2-methylpropyl)amino]-6-(quinolin-5-yl)imidazo[1,2-a]pyrazin-3-yl}benzamide (Mps-BAY2a), and N-cyclopropyl-4-{8-(isobutylamino)imidazo[1,2-a]pyrazin-3-yl}benzamide (Mps-BAY2b).

In their recent publication (published after the priority date of the present disclosure), Maachani et al. (Mol Cancer Res. 13(5):852-62 (2015)) used NMS-P715 Mps inhibitor (100 mg/kg) and showed that inhibition of Mps1 enhances radiosensitization of human glioblastoma. While the authors did not explore increase in CIN as a potential mechanism for the observed radiosensitivity, their results corroborate certain findings of the present disclosure, in particular that inhibition of protein/or molecules that promote faithful chromosome segregation leads to increased susceptibility of cancer cells to radiation therapy. Furthermore, the results observed by Maachani et al. suggest that Mps1 is required for cell survival following irradiation of GBM cells but is not required for the survival of normal cells.

Inhibition of Eg5/Kinesin as Means of Inducing CIN

Eg5, a member of the kinesin superfamily, plays a key role in mitosis, as it is required for the formation of a bipolar spindle. Eg5 controls mitosis through bipolar spindle formation and thus chromosome separation (Blangy et al. *Cell*, 83, 1159-1169 (1995)). Eg5 is overexpressed in many proliferative tissues including leukemia as well as solid tumors such as breast, lung, ovarian, bladder and pancreatic cancers (Hedge et al. Proc. Am. Soc. Clin. Oncol., 22 (2003), Ding et al. Int. J. Urol., 18, 432-438 (2011), Liu et al. J. Pathol., 221, 221-228 (2010)). Given the role that Eg5 plays in promoting faithful chromosomal segregation, the findings of the present disclosure indicate that specifically targeting and inhibiting Eg5 in cancer cells leads to radiosensitization of such cells.

Known Eg5 inhibitors include, but are not limited to 4SC-205, currently in Phase I Clinical Trial (ClinicalTrials.gov ID: NCT01065025, Open Label, Dose Escalation Trial of Oral Eg5 Kinesin-spindle Inhibitor 4SC-205 in Patients With Advanced Malignancies (AEGIS); and AZD4877, which was part of a Phase I trial in patients with solid and lymphoid malignancies (Gerecitano et al. *Invest New Drugs*. (2):355-62 (2013)). 4SC-205 was administered once or twice weekly at doses of 25 mg-200 mg. In case of AZD4877, a standard 3+3 dose-escalation design was used, where AZD4877 was given as an intravenous infusion on days 1, 4, 8 and 11 of each 21-day cycle (Gerecitano et al. *Invest New Drugs*. (2):355-62 (2013)).

Additional nonlimiting examples of specific Eg5 inhibitors include monastrol ($IC_{50}$=30 μM), enastron, dimethylenastron, S-trityl-1-cysteine (STLC), ispinesib, and HR22C16 where some of these inhibitors are currently in phase I or II clinical trials as anticancer drugs (El-Nassan H B, *Eur J Med Chem*. 62:614-31 (2013). For further details regarding Eg5 inhibitors please refer to El-Nassan H B, *Eur J Med Chem*. 62:614-31 (2013).

Additionally, specific Eg5 inhibitors have been shown to be effective against taxol-resistant cancer cells (Marcus et al. *J. Biol. Chem.*, 280 (2005)). Therefore, given the findings of the present disclosure, combining inhibition of proteins that promote faithful segregation of chromosomes with radiation therapy can offer new treatment solutions for tumors resistant to other therapies.

Inhibition of Polo-Like Kinase 4 (PLK4) as Means of Inducing CIN

PLK4 is a conserved key regulator of centriole duplication (Bettencourt-Dias et al. Curr. Biol. 15, 2199-2207 (2005)). Dysregulation of PLK4 expression causes loss of centrosome numeral integrity, which promotes genomic instability (Ganem et al. Nature 460, 278-282 (2009). Thus, in some embodiment, the present disclosure comprises the use of PLK4 inhibitors in cancer cells in order to generate cancer cells more susceptible to radiation therapy compared to cancer cells that not treated with PLK4 inhibitor prior to radiation therapy.

Small molecules that specifically target and inhibit the kinase activity of PLK4 have been identified (Mason et al., *Cancer Cell* 26, 163-176 (2014); Wong et al. *Science* 348, 1155-1160, (2015)), and one of these inhibitors, CFI-400945 is currently in phase I clinical testing (ClinicalTrials.gov Identifier: NCT01954316). CFI-400945 exhibits a PLK4 $IC_{50}$=2.8 nM, and PLK $K_i$=0.26 nM. Ongoing clinical trial study involves testing of the CFI-400945 fumarate tablets, with dose levels of 3, 6, 11, 16, 24, and 32 mg/day. In mice, CFI-400945 has been used at dosages of 2.5-20 mg/kg (Mason et al., *Cancer Cell* 26, 163-176 (2014)).

Wong et al. (*Science* 348, 1155-1160, (2015)) have recently reported 2 highly selective PLK4 inhibitors, centrinone [LCR-263; inhibition constant (Ki)=0.16 nM in vitro; centrosome depletion at 100 nM] and centrinone-B (LCR-323; Ki=0.6 nM in vitro; centrosome depletion at 500 nM).

Additionally, the PLK4 inhibitor R1530 downregulates the expression of mitotic checkpoint kinase BubR1, which in leads to polyploidy (Tovar et al. *Cell Cycle*. 9(16):3364-75 (2010)).

A more detailed discussion regarding the inhibition of PLK4 in cancer treatment is described by Holland and Cleveland. *Cancer Cell*. 26(2):151-3 (2014)).

Inhibition or Activation of Bub Kinases as Means of Inducing CIN

BubR1 and Bub1 are paralogous serine/threonine kinases that perform different functions in the spindle assembly checkpoint (SAC). BubR1 associates with unattached kinetochores, contributes to stabilizing kinetochore-MT attachments and aligning chromosomes, and forms part of the mitotic checkpoint complex (MCC). During mitosis, Bub1 binds kinetochores and plays a key role in establishing the mitotic spindle checkpoint and aligning chromosomes in addition to its central role in ensuring fidelity during chromosomal segregation into daughter cells (Yu et al. 4:262-265 (2005)). Bub1 transgenic mice develop aneuploid tumors (Ricke, et al. J. Cell Biol. 193, 1049-1064 (2011)).

Recently, Brazeau and Rosse (ACS Med Chem Lett. 5(4): 280-281 (2014)) reported a development of series of cycloalkenepyrazoles, which are able to target and specifically inhibit Bub1 kinase. Additionally, 2OH-BNPP1 is a potent inhibitor of Bub1 with $IC_{50}$s around 250 nM (Kang et al. *Mol Cell*. 32(3): 394-405. (2008), Nyati et al. *Sci Signal*. 6; 8(358) (2015)). Such agents are suitable for use in the present methods.

Down-regulation of BubR1 by oncogenic protein breast cancer-specific gene 1 (BCSG1)-mediated inhibition has been observed in advanced stage breast cancer and is believe to promote chromosomal instability (CIN). Thus, according to the present disclosure, one example of strategy suitable for radiosensitization is the inhibition of Bub1 and BubR1.

Paradoxically, reports have also suggested that BubR1 overexpression leads to high incidence of aneuploidy coupled with malignant progression (Ando et al. *Cancer Sci*. 101:639-645 (2010)). Based on the above studies, it appears that BubR1 at basal level functions to prevent missegregation of sister chromatids during mitosis, but either gain or loss of BubR1 expression promote CIN-driven tumorigenesis and cancer progression. Thus, the inventors anticipate that either inhibition of activation of BubR1, as well as Bub1 can be manipulated in order to achieve proper radiosensitization. For activation of BubR1, a small molecule agonist could be developed through a chemical screen.

Inhibition or Activation of Mad2 and Hec1 as Means of Inducing CIN

As mammalian cells proceed from prometaphase to metaphase, a signalling complex that contains mitotic arrest deficient 1(MAD1), MAD2, Mps1, BuB1, BuB3 and BuBR1 assembles at unoccupied kinetochores. Mad2 is a central component of the spindle assembly checkpoint, which is a feedback control that prevents cells with incompletely assembled spindles from leaving mitosis. Partial loss of checkpoint control, via deletion of one MAD2 allele results in a defective mitotic checkpoint in human cancer cells, leading to an increased rate of chromosome missegregation events and an increased frequency of aneuploid metaphases compared to cells control cancer cells (Michel et al. *Nature* 409, 355-359 (2001)). Thus, based on the consequences (induction of CIN) of MAD2 loss in cancer cells, as well as on the findings of the present disclosure, use of specific Mad2 inhibitors in conjunction with radiation therapy is anticipated to lead to enhanced tumor treatment response.

Recently, Kastl et al. identified a specific MAD2 inhibitor-1 (M2I-1), the first small molecule inhibitor targeting the binding of Mad2 to Cdc20, an essential protein-protein interaction (PPI) within the SAC (Kastl et al. *ACS Chem. Biol.*, 10 (7) 1661-1666 (2015)).

Hec1 (Highly Expressed in Cancer 1) is one of four proteins of the outer kinetochore Ndc80 complex involved in the dynamic interface between centromeres and spindle microtubules. Inhibition of Hec1 phosphorylation abrogates microtubule attachment to the kinetochore and induces chromosome missegregation, underscoring the importance of Hec1 phosphorylation in faithful chromosome segregation and the maintenance of genomic stability in mitosis (Du et al. *Oncogene.* 27(29):4107-14 (2008)). Thus, inhibition of Hec1 is another method by which w-CIN can be induced, leading to radiosensitization of cancer cells and tumors.

Examples of Hec1 inhibitors include, but are not limited to TAI-95 and TAI-1 (Huang et al. *Mol Cancer Ther.* 13(6):1419-30 (2014), Huang et al. *J Exp Clin Cancer Res.* 33:6, (2014)). TAI-95 is highly potent in breast cancer cell lines, with $GI_{50}$ between 14.29 and 73.65 nmol/L. Furthermore, TAI-95 showed excellent oral efficacy in an in vivo breast cancer model, where mice were treated with TAI-95 twice a day for 28 days, using TAI-95 orally at 10, 25, 50 mg/kg (mpk) or intravenously at 10, 25, 50 mpk (Huang et al. *Mol Cancer Ther.* 13(6):1419-30 (2014). In case of TAI-1, TAI-1 was shown to be effective orally in in vivo animal models of triple negative breast cancer, colon cancer and liver cancer. Furthermore, a 7-day toxicology studies of TAI-1 in mice showed no significant change in body weight, organ weight, and plasma indices when animals were treated with 7.5, 22.5, and 75.0 mg/kg twice a day by oral administration (Huang et al. *J Exp Clin Cancer Res.* 33:6, (2014).

It is important to emphasize that for certain mitotic checkpoint genes known to be implicated in tumors, such as Mad2 and Hec1, both partial inactivation and overactivation of the mitotic checkpoint promote chromosomal instability. For example, Hec1 overexpression hyperactivates the mitotic checkpoint and induces tumor formation in vivo (Diaz-Rodriguez et al. Proc Natl Acad Sci USA. 105(43): 16719-24 (2008)). Furthermore, overexpression of Hec1 resulted in lagging chromosomes and aneuploidy (Diaz-Rodriguez et al. Proc Natl Acad Sci USA. 105(43):16719-24 (2008)). Thus, in addition to the inhibition of Hec1 as a means of radiosensitization, activation or upregulation of Hec1 can also be used to promote CIN, resulting in radiosensitization. In addition to development of agents that can promote activation or cause upregulatiuon of Hec1, this can also be achieved by altering the phosphorylation patterns of Hec1, which can make Hec1 more stable, causing it to latch onto microtubules more strongly, and leading to increased stability and increased chromosome missegregation.

In addition to Hec1, Mad2 overexpression has also been shown to promote aneuploidy and tumorigenesis in mice (Sotillo et al. *Cancer Cell.* 11:9-23 (2007)). Thus, agents that cause activation of upregulation of Mad2 (and lead to checkpoint hyperactivity) can also be used to promote radiosensitization.

Noncoding RNA Activated by DNA Damage (NORAD)

Long noncoding RNAs (lncRNAs) have emerged as regulators of diverse biological processes. Recently, Lee at al. performed a functional analysis of a poorly characterized human lncRNA (LINC00657) that is induced after DNA damage, which they termed "noncoding RNA activated by DNA damage", or NORAD (Lee at al. *Cell.* 164(1-2):69-80 (2016)). The authors showed that inactivation of NORAD triggers dramatic aneuploidy in previously karyotypically stable cell lines. They further discovered that NORAD maintains genomic stability by sequestering PUMILIO proteins, which repress the stability and translation of mRNAs to which they bind.

Thus, in light of findings disclosed herein, it is anticipated that inhibition of NORAD can also be used for radiosensitization.

Antibodies Against Target Proteins

In addition to inhibitors discussed above, specific inhibition of Kif2b, MCAK, MPS1, Eg5/Kinesin-5, Polo-like kinase 4, Mad2, and Hec1 can be achieved using monoclonal or polyclonal antibodies and related specific binding moieties such as immunoreactive fragments thereof.

Table 1 lists nonlimiting examples of commercially available human-specific monoclonal or polyclonal antibodies against each of these proteins.

| Target Protein | Commercially Available Antibody (Catalog Number) |
| --- | --- |
| Kif2b | NBP1-89446 (Novus Biologicals, Littleton, CO); CPBT-38621RH (Creative Diagnostics, Shirley, NY). |
| MCAK | ab42676 (Abcam, Cambridge MA); (M01), clone 1G2 (Abnova, Walnut, CA |
| MPS1 | [N1] (ab11108) (Abcam, Cambridge, MA); (7E3) (MA5-15523) (Thermo Fisher Scientific, Waltham, MA) |
| Eg5/Kinesin-5 | 10C7/Eg5 (Bio Legend, San Diego, CA) PA5-28933 (Thermo Fisher Scientific, Waltham, MA) |
| PLK4 | [36-298] (ab17057) (Abcam, Cambridge, MA); A300-251A (Bethyl Laboratories Montgomery, TX) |
| Mad2 | ENZ-ABS169-0200 (Enzo Life Sciences, Farmingdale, NY); sc-393188 (Santa Cruz Biotechnology, Dallas, Texas) |
| Hec1 | ab3613 (Abcam, Cambridge, MA); A3 00-771A (Bethyl Laboratories Montgomery, TX) |

Threshold Levels of Inhibition or Activation of Target Protein

In previous sections, means by which target proteins can be inhibited or activated for the purposes of inducing w-CIN and consequently radiosensitization were described. In this section, the inventors provide approximate threshold levels for inhibition or activation of target genes, wherein such threshold levels are expected to provide levels of target genes sufficient for induction of w-CIN and radiosensitization. Table 2 includes approximate threshold levels for inhibition of genes that promote faithful chromosome segregation, while Table 3 provides such threshold levels for activation of genes that promote chromosome missegragation.

TABLE 2

Increase in CIN via inhibition of genes that
promote faithful chromosome segregation.

| Genes that promote faithful chromosome segregation | Threshold Levels of Inhibition |
|---|---|
| Kif2b | 1.5-fold or more |
| MCAK | 2 fold or more |
| MPS1 | 2 fold or more. Severe inhibition can result in checkpoint and arrest. |
| Eg5/Kinesin-5 | 5-fold (would need be reversible inhibition to avoid mitotic arrest in the case of non-reversible inhibition) |
| PLK4 | 2 fold or more |

TABLE 3

Increase in CIN via activation of genes
that promote chromosome missegragation.

| Genes that promote chromosome misssegregation | Threshold Levels of Activation |
|---|---|
| MAD2 | 2-3 fold |
| BUBR1 | 2-3 fold |
| HEC1 | >3-fold |

In addition to methods of inhibition discussed in prior sections, it is noted that target genes and proteins can be reduced or inhibited at any level, including the protein, RNA, or DNA level. Furthermore, any techniques known in the art that are used for reducing protein, RNA, or DNA levels can be used to achieve increase in w-CIN and radiosensitization. Such techniques include, but are not limited to gene deletion, gene disruption, shRNA or antisense approaches. Additionally, gene modification (gene editing) can be achieved using an engineered nuclease such as a zinc finger nuclease (ZFP), TALE-nuclease (TALEN), or CRISPR/Cas nuclease.

Kif2b and MCAK as Radioprotective Agents

Activation or overexpression of proteins that promote faithful chromosome segregation can be used as a method of protection of noncancerous cells against radiation. Since overexpression of Kif2b results in decreased CIN, agents that activate or upregulate Kif2b can be used as radioprotectors. Such radioprotectors can serve to protect noncancerous cells preferentially as the radiation intensity is focused on the tumor (e.g., in conformal radiation), making any radioprotector in the tumor cells practically ineffective. Furthermore, radioprotectors can alternatively be used to shield and protect organs or tissues. For example, the digestive tract can be protected by delivering a radioprotector that is not systemically absorbed but it can have a topical or local effect on the tract, which tends to receive the most damage of ionizing radiation. Such organs include, but are not limited to the pharynx, esophagus, stomach, small and large intestines, and rectum. This approach to tissue protection can also be applied to other mucosal surface such as the vaginal tract and the cervix.

Based on the findings of the present disclosure, it is anticipated that any agent that specifically promotes faithful chromosome segregation, and reduction in lagging chromosomes and/or CIN could be used as a radioprotective agent. The inventors reserve the right to disclaim any agent disclosed herein, radiosensitizing or radioprotective, that is deemed to deprive the claimed invention of novelty or inventiveness (render it obvious).

Methods for Detection of w-CIN

The CIN status of tumors is not routinely evaluated in the clinical setting even though a large amount of data collected from human tumors suggests that aneuploidy has a causative role in tumorigenesis by showing that CIN and chromosomal aberrations correlate with tumor grade (Carter et al. Nature Genet. 38, 1043-1048 (2006), Kronenwett, U. et al. Cancer Res. 64, 904-909 (2004)).

Fluorescence in situ hybridization (FISH) is one of the main methods for the assessment of w-CIN status in tumors. Variations in chromosome copy number across the cell population can be quantified using fluorescently labeled DNA probes that bind to the centromeres of specific chromosomes. FISH thus allows the assessment of the chromosomal state of hundreds of cells, and the rate of change can be inferred from the cell-to-cell variability in chromosome number (Speicer et al. Nat Rev Genet 6: 782-792 (2005)).

Additional methods for assessing w-CIN status include, but are not limited to flow and DNA image cytometry. These methods have been discussed by Darzynkiewicz et al. Adv Exp Med Biol 676: 137-147 (2010)). Both of these methods measure cellular DNA content through the use of dyes that bind stoichiometrically to DNA, allowing DNA cell cycle distribution and ploidy to be determined. The ability of cytometry techniques to identify w-CIN in tumors is supported by the observation that anaphase bridges are only observed in tumors defined as CIN by cytometry in a small cohort of sarcomas, colorectal and pancreatic carcinomas (Fiegler et al., Nucleic Acids Res 35: e15 (2007)).

Single-cell, comparative genomic hybridization (CGH) (Fiegler et al., Nucleic Acids Res 35: e15 (2007)) can yield information on both numerical and structural chromosomal aberrations at a single-cell level, and heterogeneity can then be quantified by comparing multiple cells. Karyotypic complexity measures of CIN are commonly performed on a combined population of cells. Conventional array CGH uses DNA from multiple cells, and can be used to define the both structural chromosomal complexity and copy number changes in a tumor sample (Pinkel et al. Nat Genet 37: S11-S17 (2005)).

Methods for w-CIN assessment are discussed in detail by McGranahan et al. *EMBO Rep.* 13(6): 528-538 (2012)). Chromosoaml instability can also be assessed directly by measuring the frequency of lagging chromosomes in dividing cells undergoing anaphase or telophase. This has been shown in Diffuse Large B Cell Lymphoma as well as rectal cancer but is viable in most tumor specimens where surgical or core biopsies or excision exist and the tissue is either stained using standard Hematoxylin and Eosin staining, immunofluorescence or immunohistochemistry. In the following two papers, the method was used as a prognostic and predictive marker. See for example" Clin Cancer Res. 2011 Dec. 15; 17(24): 7704-11. doi: 10.1158/1078-0432.CCR-11-2049.

Figure 1B:
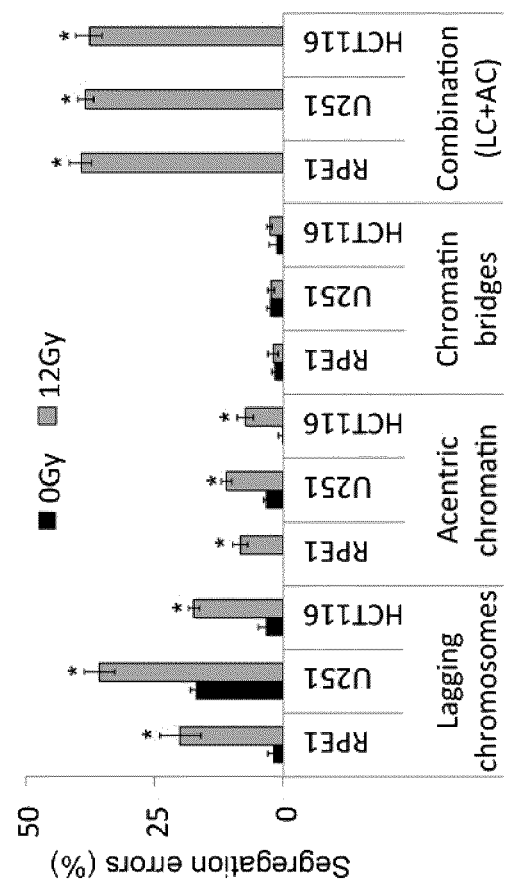

Chromosomal instability substantiates poor prognosis in patients with diffuse large B-cell lymphoma. Bakhoum SF1, Danilova O V, Kaur P, Levy N B, Compton D A. See also, Cancer. 2014 Jun. 1; 120(11):1733-42. doi: 10.1002/cncr.28656. Epub 2014 Mar. 6. Chromosomal instability portends superior response of rectal adenocarcinoma to chemoradiation therapy. Zaki BI1, Suriawinata A A, Eastman A R, Garner K M, Bakhoum S F As described above and as illustrated in the Examples below, the present disclosure provides novel insights into genome damage induced by IR, beyond direct DNA breaks, which damage occurs outside of the primary nucleus. The inventors have shown that when IR is delivered to mitotic cells, it can directly lead to errors in whole-chromosome segregation, which subsequently leads to the formation of micronuclei and chromosome pulverization hours to days later (FIG. 6I). The type of missegregation errors in irradiated cells are dependent on the time lapsed after IR exposure. This is likely dependent on the phase of the cell cycle during which cells are irradiated. IR exposure during interphase (G1, S and G2) of the cell cycle would produce DSBs (double strand breaks), which lead to acentric chromatin and chromatin bridges during the subsequent anaphase. This explains the prevalence of chromatin bridges and acentric chromatin 12 h after IR exposure (FIG. 1B). On the other hand, when cells are irradiated during mitosis this directly leads to the formation of lagging chromosomes. Interestingly, analysis of anaphase spindles 24 h, and up to 1 month, after IR exposure reveals chromosome missegregation patterns suggestive of both w-CIN and s-CIN. This mirrors recent work showing that w-CIN and s-CIN coexist in an interdependent manner (Crasta et al. Nature. 482:53-58, 2012), Bakhoum et al. Cancer Discov.4:1281-1289 (2014).

The multilayered genomic damage described herein provides an explanation for the exquisite sensitivity of mitotic cells to IR (Gunderson et al. Clinical Radiation Oncology. Churchill Livingstone; 2011, Terasima et al. Biophys J. 1963; 3:11-33, whereby IR exposure during mitosis not only leads to direct DNA breaks but also to additional numerical and downstream structural chromosomal damage. This cell cycle-dependent sensitivity has been exploited in the way radiation treatment is delivered in clinical settings. A fundamental rationale for dividing radiation treatment dose into small daily fractions is to enact lethal damage onto the sensitive subpopulation of tumor cells, including the mitotic subpopulation, while sparing toxicity to the surrounding normal tissue which typically contains fewer mitotic cells and is more adept at DNA repair (Gunderson et al. Clinical Radiation Oncology. Churchill Livingstone; 2011. Therefore, fractionated radiation therapy can maximize damage to mitotic cell population in otherwise non-synchronized tumors.

The magnitude of the effect of Kif2b overexpression in vivo (Example 8) is surprising given the fact that most of the tumor cell population is not in M-phase. The inventors postulate that some of this may be accounted for by the fractionation scheme under which radiation therapy was delivered. Second, when U251 cells were irradiated in vivo they exhibited an increased rate of atypical mitoses (FIGS. 6H, and 6I). These spindle defects are likely caused by pre-mitotic damage as direct IR exposure during mitosis has not been shown to significantly alter spindle geometry (Bakhoum S F, Cancer Discov. 2014; 4:1281-1289). The mechanism of how pre-mitotic irradiation induces spindle damage is poorly understood. Nonetheless, these atypical spindle geometries have been shown to lead to chromosome segregation errors (Ganem N J, Nature. 460:278-282 (2009); Silkworth et al. PLoS One. 4:e6564 (2009)). Thus, it is conceivable that the effect of Kif2b overexpression in vivo extends beyond the directly irradiated mitotic tumour subpopulation whereby Kif2b suppresses w-CIN indirectly caused by defects in spindle geometry originating from pre-mitotic damage. This hypothesis is supported by the observation that DNA damage-induced cell death is enhanced by progression through mitosis (Varmark Cell Cycle. 8:2951-2963 (2009)) and the inventors propose that this is partly due to numerical chromosomal aberration resulting from mitotic chromosome missegregation.

The dependence of irradiated mitotic cell sensitivity on chromosome missegregation rates offers insight into recent findings where patients diagnosed with rectal adenocarcinoma with elevated pre-treatment chromosome segregation errors were more likely to respond to chemoradiation therapy (Zaki et al. Cancer. 120:1733-1742 (2014)). Interestingly, in this patient cohort, there was a synergistic relationship in the predictive power between chromosome missegregation and levels of Mre11, a component of the MRN complex involved in the recognition and repair of DSBs (van den Bosch et al. EMBO Rep.4:844-849 (2003). Patients with elevated chromosome missegregation and reduced levels of Mre11 were significantly more likely to respond to chemoradiation therapy (Zaki et al. Cancer. 120:1733-1742 (2014). This indicates that increasing chromosome missegregation rates in mitosis may increase the therapeutic potency of IR particularly in the setting of decreased repair efficiency of DSBs. Such an approach may already be within clinical feasibility as several known chemotherapeutics can increase chromosome missegregation rates (Thompson et al. J Cell Biol. 188:369-381 (2010), Bakhoum et al. J Clin Invest. 122:1138-1143 (2012), Janssen et al. Proc Natl Acad Sci USA. 106:19108-19113 (2009). It can also be achieved more selectively by developing molecularly targeted inhibitors of the kinesin-13 proteins, Kif2b or MCAK, as discussed in details in the present disclosure.

The severe structural damage caused by the effect of IR on mitotic cells has important consequences on the small subset of cells that survive radiation treatment. Chromosome pulverization has been postulated to represent a precursor to massive chromosomal rearrangements known as chromothripsis (Stephens et al. Cell. 144:27-40 (2011)). The findings of the present disclosure indicate that pulverization is likely deleterious to cellular viability. In rare instances, however, these punctuated genomic alterations could lead to selective advantage and generate highly aggressive tumors, which represent a rare but devastating late side-effect of radiation therapy. In conclusion, work described in the present disclosure suggests that chromosome pulverization and subsequent chromothripsis would be a defining feature of radiation-induced secondary tumors.

EXAMPLES

Materials and Methods:
Cell Culture and Irradiation.

Cells were maintained at 37° C. in a 5% $CO_2$ atmosphere in Dulbecco's modified medium (DMEM, for U251) or McCoy's medium (for HCT116) with 10% fetal bovine serum, 50 IU ml$^{-1}$ penicillin, and 50 mg ml$^{-1}$ streptomycin. U251 cells were kindly provided from the laboratory of Mark A. Israel (Geisel School of Medicine at Dartmouth), HCT116 cells (both p53$^{+/+}$ and p53$^{-/-}$ were kindly provided by the laboratory of Bert Vogelstein (Johns Hopkins University). For plasmid selection, cells were maintained in 0.5-1.0 mg ml$^{-1}$ of G418 (geneticin). Cells were g-irradiated using a $^{137}$Cs-irradiator at a rate of 2.38Gy/min or using external beam radiation at 6 MeV delivered by a linear accelerator according to safety rules of Dartmouth and UCSF.

Antibodies.

Tubulin-specific mAb DM1α (Sigma-Aldrich), Anti-centromere antibody (CREST, Dartmouth), Anti-cleaved caspase-3 antibody (Cell Signaling), anti-Ki67-antibody (Ventana), anti-g-H2AX-antibody (Novus Biologicals), GFP-specific antibody (William Wickner, Dartmouth). Antibodies were used at dilutions of 1:1000 or 1:10000 (for GFP-specific antibody).

Immunofluorescence Imaging.

Cells were fixed with 3.5% paraformaldehyde or methanol (−20° C.) for 15 minutes, washed with Tris-buffered saline with 5% bovine serum albumin (TBS-BSA) and 0.5% Triton X-100 for 5 minutes, and TBS-BSA for 5 minutes. Antibodies were diluted in TBS-BSA+0.1% Triton X-100 and coverslips incubated for 3 hours at room temperature, then washed with TBS-BSA for 5 minutes. Secondary antibodies were diluted in TBS-BSA+0.1% Triton X-100 and coverslips incubated for 1 hour at room temperature. Images were acquired with Orca-ER Hamamatsu cooled CCD camera mounted on an Eclipse TE 2000-E Nikon microscope. 0.2 µm optical sections in the z-axis were collected with a plan Apo 60×1.4 NA oil immersion objective at room temperature. Iterative restoration was performed using Phylum Live software (Improvision). Quantification of g-H2AX fluorescence levels were done using Phylum.

Immunoblots.

Figure 10:
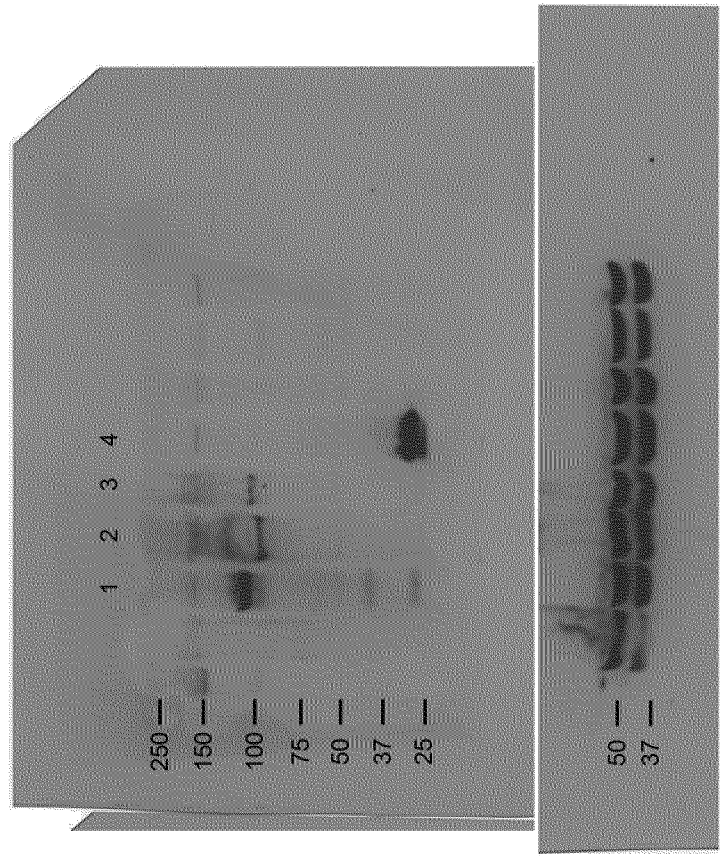
FIG. 10 is an autoradiograph of a Western blot showing Kinesin-13 overexpression in U251 cells. Upper autoradiograph is a Western blot of U251 cells expressing GFP-tagged kinesin-13 proteins Kif2b (lane 1), Kif2b (lane 2), MCAK (lane 3), and GFP (lane 4) stained using anti-GFP antibodies. DM1-α antibody was used to blot for α-tubulin as a loading control (lower autoradiograph). Molecular weight markers (in kDa) are depicted on the left side of the immunoblots.

Membranes were blocked with 0.5% milk in TBS+0.1% Tween for 1 hour. Membranes were blotted at room temperature for 3 hours with antibodies at 1:1000. Secondary HRP-conjugated anti-mouse/rabbit (BioRad) were used at 1:2000. Images of uncropped immunoblots are depicted in FIG. 10. Western blots of U251 cells expressing GFP-tagged kinesin-13 proteins Kif2b (lane 1), Kif2b (lane 2), MCAK (lane 3), and GFP (lane 4) stained using anti-GFP antibodies. DM1-α antibody was used to blot for α-tubulin as a loading control. Molecular weight markers (in kDa) are depicted on the left side of the immunoblots (FIG. 10).

Fluorescence In Situ Hybridization.

HCT116 p53−/− cells were treated with 100 µM monastrol or DMSO control for 8 h and then γ-irradiated. Immediately following irradiation, cells were washed with PBS twice and then recovered in fresh media for 1 h. For FISH analysis, cells were collected by trypsinization, briefly resuspended in 75 mM potassium chloride, fixed, washed twice in 3:1 methanol/acetic acid mix, dropped onto wet slides, air dried, and stained with DAPI. FISH was performed using both α-satellite and subtelomere probes specific for the centromeric and q arm telomeric regions of chromosomes 2 respectively (Cytocell). Cells were hybridized according to the manufacturer's protocol, and chromosome signals in at least 300 nuclei were scored.

In Vivo Xenograft HCT116 Experiments

Animal experiments were approved by Institutional Animal Cancer and Use Committee at UCSF, in accordance with institutional and national guidelines. 2-5 million HCT116 p53$^{−/−}$ cells[43] were implanted subcutaneously into the flanks of CD1-Nude mice (4-6 week-old males supplied by the UCSF Breeding Core or Jackson Labs). Tumors were measured with calipers. Volume was calculated by the following formula: width$^2$×length×0.5. Tumors were exposed to gamma irradiation ($^{137}$Cs) at fractionated doses (5 consecutive days×2Gy) when tumors were ~300 mm$^3$ or at a single dose (1 day×10Gy) when tumors were ~800 mm$^3$. Tumors were isolated and cultured or sectioned for immunohistochemistry.

Clonogenic Assays

Cells were either trypsinized (for non-synchronized populations) or collected using mitotic shake-off (for mitotic population) serially diluted and irradiated in their native medium. Cells were then plated in 25-cm$^2$ T-flasks and clones were grown for 18 days. Clones were stained with Crystal violet and colonies were counted when they reached an approximate size of ~50 cell/clone[29]. Relative viability was determined based on the 0 Gy dose.

Automated Counting of g-H2AX Foci.

Cell Profiler 2.0 (Broad Institute)[44] was used to segment nuclei and for automated counting of foci using the examplesspeckles.cp pipeline. Nuclei were segmented based on their shape and signal intensity, foci were identified based on their intensity and their diameter. Intensity threshold spanned 2.5-100%.

In Vivo Orthotopic U251 Experiments

Mouse experiments were approved by and performed according to the guidelines of the Institutional Animal Cancer and Use Committee at UCSF. U251-GFP-Kif2b cells and U251-GFP cells were modified using lentivirus expressing firefly luciferase. Dissociated cells were resuspended in ice-cold DME H-21 medium without supplements at 100, 000 cells/ml. 300,000 cells per animal were injected into six weeks old athymic mice using the Stoelting stereotactic injection apparatus and a sharp Hamilton syringe. Mice were anesthetized with isofluorane and placed in the stereotactic frame using ear bars and constant isofluorane supply through a mouthpiece adaptor. A hole was bored in the skull 1 mm anterior and 0.5 lateral to the Bregma, and 2.5 mm below the surface of the brain and cells were injected using manual pressure. Mice were followed by bioluminescence imaging until luminescence signal indicated that tumors were established. Radiation was administered at 4Gy using the JLShepherd @ Associates irradiator (model: MK1-68) three times per week, followed by bioluminescence imaging one day after each treatment. On day 13 after treatment start mice were sacrificed, perfused with 4% paraformaldehyde, brains were isolated and fixed overnight in 4% PFA, then transferred to 70% Ethanol for processing. Mouse brain specimens were serially sectioned and paraffin embedded using standard methods. H&E sections were prepared by routine methods. Antigen retrieval for immunohistochemistry was performed in Tris EDTA pH 8.0 for 30 minutes at 95 degrees Celsius. Slides were treated with blocking reagent (Vector M.O.M. kit BMK-2202) for 32 minutes. Immunohistochemistry was performed using primary antibodies for Ki67 (Ventana RRF 790-4286, undiluted, room temperature for 16 minutes) or cleaved caspase 3 (Cell Signaling #9661, diluted 1:50 in M.O.M. diluent, 37 degrees Celsius for 60 minutes). Antibody detection was performed using the Ventana IView Detection Kit (760-091).

Example 1

Ionizing Radiation Leads to Numerical Chromosomal Instability In Vitro

Figure 7A:
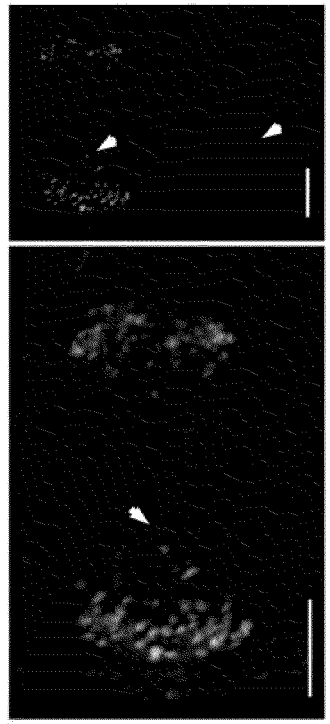
FIGS. 7A-7C illustrate chromosome segregation errors in irradiated mitotic cells.
Figure 7B:
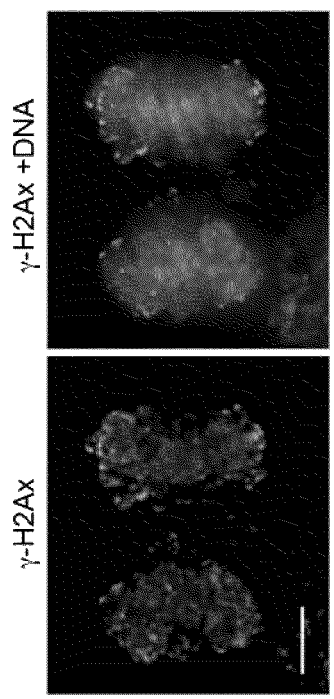

High-resolution fluorescence microscopy was used to examine various types of errors during anaphase in three human cell lines derived from normal human retinal epithelium (RPE1), colorectal cancer (HCT116) or glioma (U251). These cells were either near-diploid and chromosomally stable (RPE and HCT116) or aneuploid and chromosomally unstable (U251). RPE1 and HCT116 had an intact p53-signalling pathway (Thompson et al. *Cell Biol.* 2010; 188: 369-381, whereas U251 contain defective p53 signalling (Gomez-Godinez et al. Nucleic Acids Res. 38:e202-e202. (2010). Briefly, cells were exposed to various doses of IR and evaluated 25 minutes later for signs of chromosome segregation during anaphase. 25 minutes provided sufficient time for many of the cells that were in mitosis during DNA damage induction to enter anaphase, but not sufficient time for cells that were in G2 to proceed through to anaphase. High-resolution fluorescence microscopy revealed that IR exposure leads to a significant increase in anaphase spindles with lagging chromosomes, acentric chromatin fragments, or both (FIGS. 1A and 1B). FIG. 1A displays U251 cells fixed 25 minutes following exposure to 12 Gy and stained for centromeres using anti-centromere antibody (white dots), and DNA using (light grey cloud). As demonstrated in FIG. 1A, U251 cells exhibited lagging chromosomes (LC), chromatin bridges (CB), acentric chromatin (AC), or a combination (LC+AC). FIG. 1B shows percentages of chromosome missegregation in response to 0 or 12 Gy IR dose in anaphase spindles of RPE1, U251, and HCT116 cells. The legging chromosomes evaluated after IR exposure displayed centromere staining and maintained attachments to microtubules emanating from opposite spindle poles (FIG. 7A). Furthermore, these legging chromosomes exhibited similar levels of staining of γ-H2AX, a marker of DNA double stand breaks (DSBs), compared with the remaining chromosomes (FIG. 7B). Additionally, the inventors did not observe significant increase in spindles with chromatin bridges (FIGS. 1A-B).

Figure 1C:
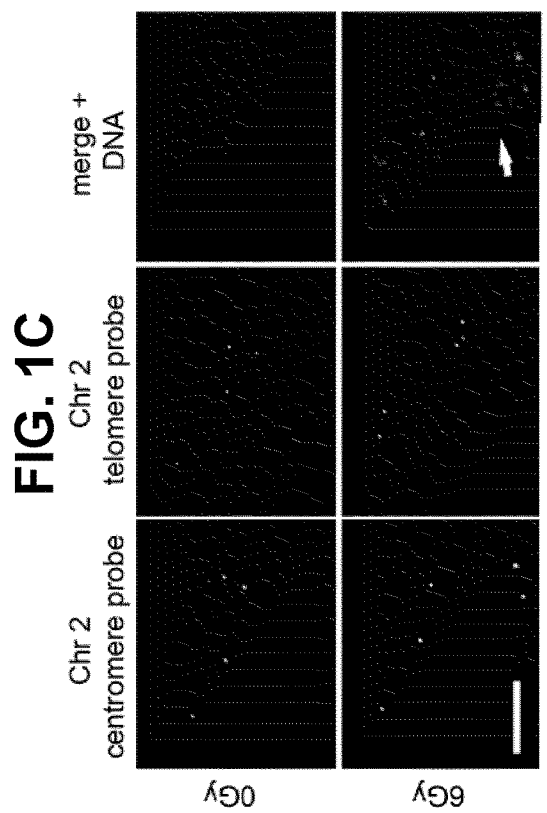
Figure 1D:
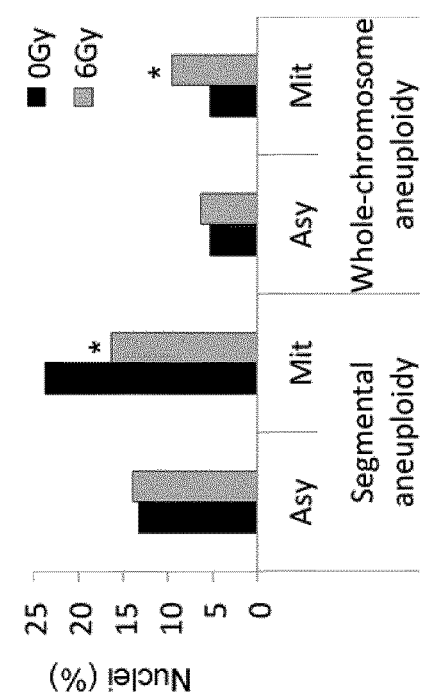

Consequences of IR exposure on chromosome segregation were further evaluated by exposure of HCT116 cells to 6 Gy, followed by fluorescence in situ hybridization (FISH) using centromere and telomere probes for chromosome 2 on irradiated nuclei 1 hour later. As shown in FIG. 1C, exposure of non-synchronized cells to IR did not result in significant short-term change in chromosome number. However, when the cells were enriched for mitotic cells using a mitotic shake-off method, IR exposure resulted in approximately 2 fold increase in aneuploidy as evidenced by balanced changes in both centromere and telomere probes specific to human chromosome 2 (FIG. 1D).

Example 2

Figure 1E:
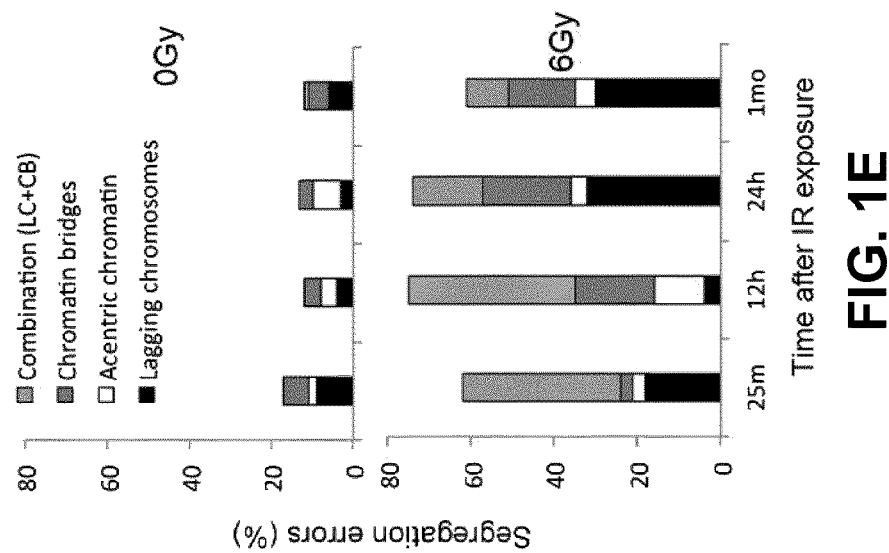

Frequency and Type of Chromosome Segregation Error is Dependent on the Time Interval Between Radiation and Chromosome Segregation Analysis The inventors sought out to evaluate whether the frequency and types of chromosome segregation errors are dependent on the time interval between IR exposure and the analysis of anaphase chromosome segregation. HCCT116 cells devoid of tumor suppressor, p53, were used in this experiment, to allow for the proliferation of aneuploidy cells should they emerge (Thompson and Compton, *J Cell Biol.* 188(3):369-81, 2010). HCT116 p53-/- cells were exposed to 0 or 6 Gy of IR and chromosome segregation errors were evaluated at 25 minutes, 12 h, 25 h, and 1 month following the IR exposure. As shown in FIG. 1E, anaphase spindles examined 25 minutes after irradiation exhibited similar chromosome missegregation profiles compared with p53-competent HCT116 cells 25 minutes after IR exposure. However, 12 h after irradiation there was a significant increase in chromatin bridges and acentric chromatin fragments but not lagging chromosomes (FIG. 1E). Interestingly, anaphase spindles examined 24 h or up to 1 month after IR exposure revealed a significant increase in both lagging chromosomes and chromatin bridges (FIG. 1E). These findings indicate that chromosome segregation errors in response to IR exposure are time dependent, where lagging chromosomes peak shortly (25 min) after IR exposure, whereas chromatin bridges peak 12 h later. Importantly, long-term examination (after 1 month) of irradiated cells shows persistence of lagging chromosomes and chromatin bridges, the hallmarks of w-CIN and s-CIN, respectively.

Example 3

IR Induces w-CIN In Vivo

To determine whether IR can directly perturb the process of chromosome segregation in vivo, the inventors used tumour-forming HCT116 p53-/- cells that normally exhibit low rates of chromosomes missegregation and are thus considered chromosomally stable and near-diploid (Thompson and Compton, *J Cell Biol.* 188(3):369-81, 2010). HCT116 p53-/- cells were subcutaneously injected into nude mice and after 25 days transplanted tumours were exposed to 0 or 10 Gy of IR. Following formalin-fixation of tumours 25 min later, tumour sections were stained with hematoxylin and eosin and the effects of radiation on mitotic cells were evaluated (FIGS. 2A-B). FIG. 2B shows an example of normal anaphase and anaphase cells containing lagging chromosomes in HCT116 p53-/- xenografts after IR exposure. As demonstrated in FIG. 2C, tumours exposed to 10 Gy of IR exhibited significantly higher rates of chromosome segregation errors during anaphase compared with control, non-irradiated, tumours. In tumours from irradiated animals, haematoxylin-stained chromatin was frequently visible in the central spindle during anaphase (FIG. 2B and insets). This chromatin often contained a central constriction reminiscent of centromeric DNA suggesting that this chromatin encompassed whole chromosomes. However, experimental limitations preclude us from resolving lagging chromosomes from acentric chromatin fragments with absolute certainty in fixed tumour tissues.

To study the effects of IR on HCT116 p53-/- xenografts in further detail, HCT116 p53-/- xenografts were exposed to varying doses of radiation (0 Gy, 10 Gy and five daily fractions of 2 Gy over 5 consecutive days (FIG. 2D)). As mitotic cells represent a minority of the tumour cell population at any given time, the latter fractionated regimen (2 Gy×5 days) aims at targeting an overall larger number of mitotic cells over consecutive days. Cells were subsequently derived from irradiated tumours and passaged in culture for an additional 15 days to obtain sufficient numbers of cells for karyotype analysis (FIG. 2D). Cells derived from non-irradiated tumours displayed mitotic spreads with near-diploid karyotypes. In contrast, mitotic spreads of cells derived from irradiated tumours showed significant deviations from the near-diploid modal chromosome number—particularly those exposed to five daily fractions (FIG. 2E). There was also a small increase in near-tetraploid cells, which appeared to have undergone a genome-doubling event (FIG. 2E).

Example 4

Extra-Nuclear DNA Damage in Irradiated Mitotic Cells

In addition to aneuploidy, lagging chromosomes can lead to downstream defects that culminate in structural chromosomal damage (Hatch et al. *Cell.* 154:47-60, 2013), such as the exclusion of lagging chromosomes from the primary nucleus in the subsequent G1 phase of the cell cycle, resulting in the formation of micronuclei. RPE1 and U251 cells examined 12 h after IR exposure showed increased frequencies of whole-chromosome-containing micronuclei that positively stained for both DNA and centromeres (FIGS. 3A-C).

Next, mitotic U251 cells obtained by mitotic shake-off were irradiated with 12 Gy and chromosome spreads examined 24 h after irradiation in order to assay for chromosome pulverization in the subsequent mitosis as previously described by Crasta et al. (*Nature.* 482:53-58, 2012) (FIG. 3D). In these spreads, the appearance of many small chromosome fragments and decondensed chromatin indicate the consequences of chromosome pulverization (FIG. 3E). As shown in FIG. 3F, 12 Gy of IR to mitotic U251 cells led to a significant increase in the fraction of chromosome spreads displaying pulverized chromosomes.

To assess the relative levels of DNA damage in the micronuclei compared with the primary nuclei, the fluorescence density of γ-H2AX was evaluated. Without irradiation both primary nuclei and micronuclei had equivalent densities of γ-H2AX fluorescence, which then significantly increased 25 min after IR exposure. As shown in FIGS. 3G and 3H, γ-H2AX density in primary nuclei was significantly lower 12 h after IR exposure compared with 25 min, congruent with DNA repair activity. Conversely, γ-H2AX density in micronuclei was significantly increased at 12 h as compared with 25 min after IR exposure (FIGS. 3G-H). These findings indicate that micronuclei are not only defective in DNA repair but can actively generate additional DNA damage. This additional damage is likely the consequence of faulty attempts at DNA repair and defective micronuclei nuclear envelope structures. Therefore, by inducing mitotic errors, IR leads to amplifications of structural chromosomal defects that predominantly occur outside of the primary nucleus (extra-nuclear). Unlike DNA damage caused directly by IR, these defects are precipitated many hours after IR exposure.

Example 5

Figure 7C:
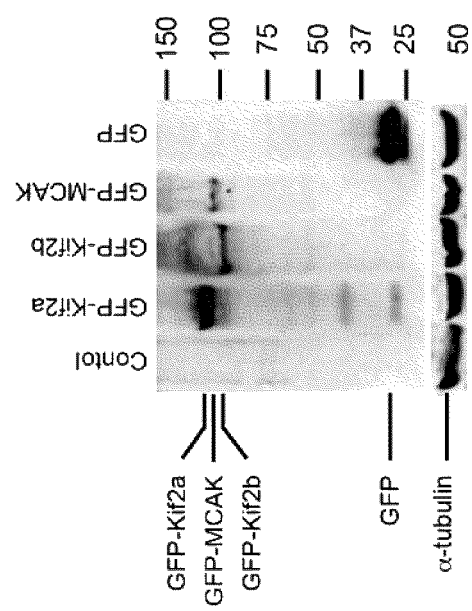

Extra-Nuclear Chromosomal Damage Occurs as a Result of Mitotic Chromosome Segregation Errors To corroborate the findings from Example 4, which indicate that extra-nuclear chromosomal damage occurs as a result of mitotic chromosome segregation errors, lagging chromosomes were measured 25 min after irradiation (0, 2, 6, and 12 Gy) in U251 cells overexpressing GFP-Kif2b (FIG. 3I, FIG. 7C). Kif2b is a microtubule-depolymerizing kinesin-13 protein that specifically corrects erroneous microtubule attachments to chromosomes (Bakhoum et al. Nat Cell Biol. 2009; 11:27-35; Manning et al. *Mol Biol Cell.* 2007; 18:2970-2979). Its overexpression was shown to selectively reduce whole-chromosome segregation errors and suppression of w-CIN in clonogenic assays in many cancer cell lines, including U251 cells (Bakhoum et al. Nat Cell Biol. 2009; 11:27-35). It does so by reducing the stability of microtubule attachments to chromosomes at kinetochores, which are frequently elevated in chromosomally unstable cancer cell lines (Bakhoum et al. Curr Biol. 2009; 19:1937-1942).

As shown in FIG. 3I, U251 cells overexpressing GFP-Kif2b displayed greater than twofold reduction in chromosome segregation errors during anaphase compared with control U251 cells, as well as fewer chromosome segregation errors during anaphase after IR exposure. (FIG. 3I). In similar experiments, we found that GFP-Kif2b overexpression reduced the frequency of IR-induced lagging chromosomes in otherwise chromosomally stable RPE1 cells (Bakhoum Cancer Discov. 2014; 4:1281-1289). Accordingly, GFP-Kif2b overexpression also led to significant reductions in the frequency of cells containing micronuclei in both RPE1 and U251 cells (FIG. 3C). We then examined mitotic spreads, 24 h after exposure of mitotic cells to IR, for downstream chromosomal breaks known to result from micronuclei.

Next, 24 hours after exposure of mitotic cells to IR, mitotic spreads were evaluated for downstream chromosomal breaks known to result from micronuclei. As demonstrated in FIG. 3F, GFP-Kif2b overexpression significantly reduced the incidence of spreads with pulverized chromosomes. This was not a complete suppression, indicating that chromosome pulverization in response to IR may also occur through alternative pathways unrelated to lagging chromosomes.

Example 6

Kif2b Overexpression does not Alter IR-Induced DNA Breaks or Repair

Figure 4A:
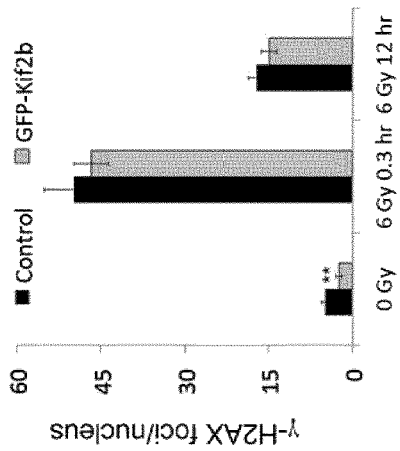
FIGS. 4A-4C show that Kif2b overexpression does not alter IR-induced DNA breaks or repair.
Figure 4B:
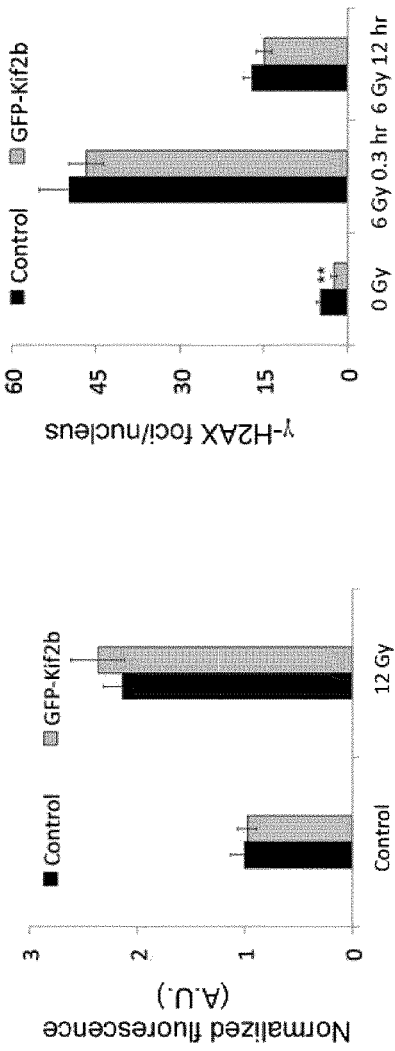
Figure 4C:
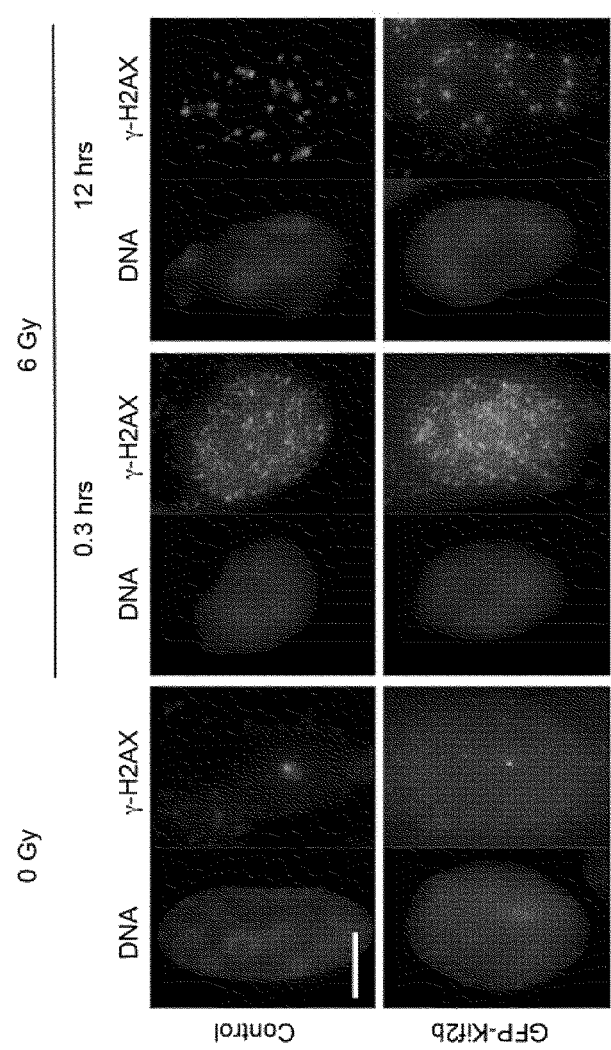

In order to ensure that GFP-Kif2b overexpression does not alter the formation of direct DSBs in irradiated cells or the influence their ability to repair these breaks in primary nuclei, the inventors measured relative γ-H2AX fluorescence intensity in irradiated mitotic U251 cells. As shown in FIG. 4A, there was no difference between control and GFP-Kif2b-overexpressing U251 cells. Furthermore, when the average number of γ-H2AX foci in the primary nuclei 20 min after IR exposure was compared to that of 12 h after IR exposure, there was no significant difference between control and GFP-Kif2b-overexpressing cells (FIGS. 4B-C). As expected, there was an approximately threefold decrease in the number of γ-H2AX foci 12 h following irradiation in both conditions, owing to DNA DSB repair activity (FIGS. 4B-C). These findings indicate that suppression of mitotic errors reduces extra-nuclear chromosomal defects without significantly altering the incidence of DNA DSBs in the primary nucleus or the rate at which they are repaired.

Example 7 w-CIN Influences Viability of Irradiated Mitotic Cells

Mitosis has long been recognized, for unclear reasons, as the most radiation sensitive phase of the cell cycle (Terasima et al. Biophys J. 1963; 3:11-33; Sinclair et al. Radiat Res. 1966; 29:450-474). In previous Examples, the inventors have accomplished to selectively reduce chromosome segregation errors without influencing the canonical IR-induced DNA damage and repair within the primary nucleus. This allows for testing whether whole-chromosome segregation errors might independently contribute towards the sensitivity of mitotic cells to IR.

Figure 5B:
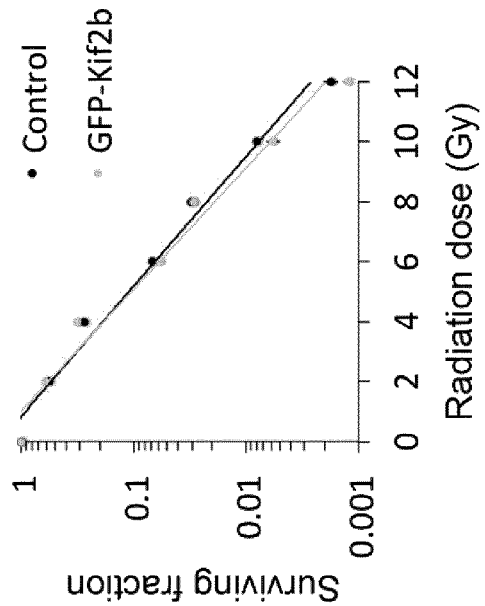
FIGS. 5A-5B show that chromosome segregation errors alter the viability of irradiated mitotic cells.
Figure 5A:
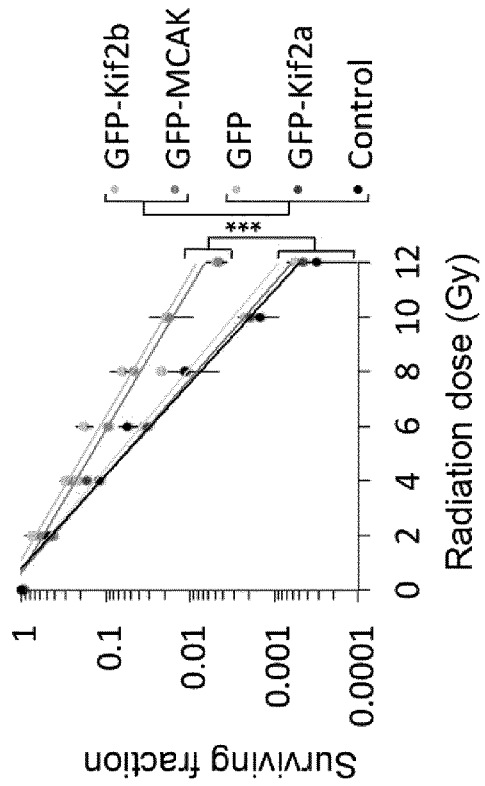
Figure 8C:
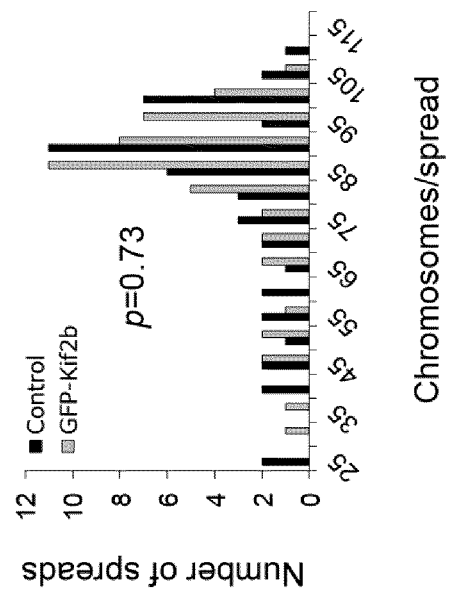
FIGS. 8A-8C show that overexpression of Kif2b alters viability of irradiated mitotic cells without altering basal growth rates or ploidy in culture.
Figure 8A:
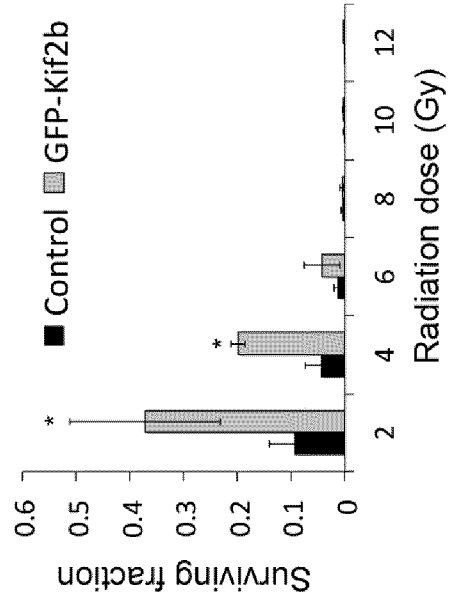
Figure 8B:
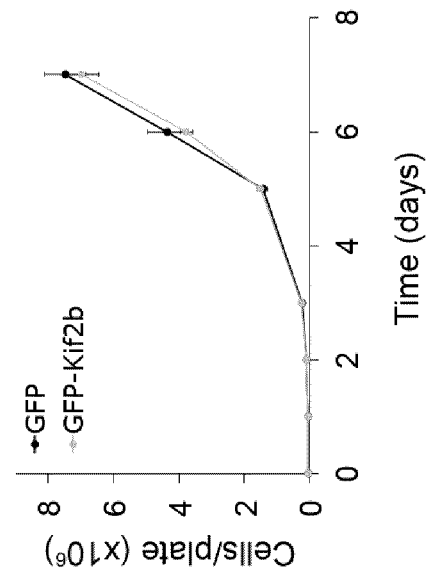

Next, the inventors tested the colony-forming ability of U251 cells over-expressing GFP, GFP-Kif2b, GFP-Kif2a, or GFP-MCAK after exposure of cells to 0, 2, 4, 6, 8, 10, and 12 Gy. In order to focus on the potential effects of radiation on cells during mitosis, cells were enriched for mitotic cells using mitotic shake-off before irradiation and plating for colony growth (FIG. 5A). As shown in FIG. 5A, GFP-Kif2b overexpression led to significant increase in the viability after irradiation, whereby at 12 Gy of IR, these cells were ~20-fold more resistant compared with control cells. Similar to the results observed in U251 cells, GFP-Kif2b overexpression led to increased viability in RPE1 cells as well (FIG. 8A). Importantly, GFP-Kif2b overexpression did not alter the growth rate of U251 cells in culture or did it significantly influence their karyotypic distribution or modal chromosome numbers (FIG. 8B, 8C).

Additionally, overexpression of GFP-MCAK, a second kinesin-13 protein also known to suppress w-CIN, led to a similar increase in clonogenic viability of mitotic U251 and RPE1 cells (FIG. 5A and FIG. 7C). On the contrary, overexpression of either GFP alone or the third microtubule-depolymerizing kinesin-13 paralogue, GFP-Kif2a, which does not reduce chromosome segregation errors during mitosis (Bakhoum et al. *Nat. Cell Biol.* 11, 27-35 (2009)), did not alter the clonogenic potential of irradiated cells compared with control (FIGS. 5A and 7C). Interestingly, when U251 cells were irradiated with 0, 2, 4, 6, 8, 10, or 12 Gy as a non-synchronized population that contains only a small fraction of mitotic cells, overexpression of GFP-Kif2b did not influence the colony-forming ability (FIG. 5B). Collectively, these results indicate that chromosome segregation errors impact the viability of irradiated mitotic cells as the selective suppression of these errors through destabilization of kinetochore-microtubule stability leads to significant increase in mitotic cell resistance to IR.

Example 8

Suppressing w-CIN Leads to Tumour Radiation Resistance

Figure 9:
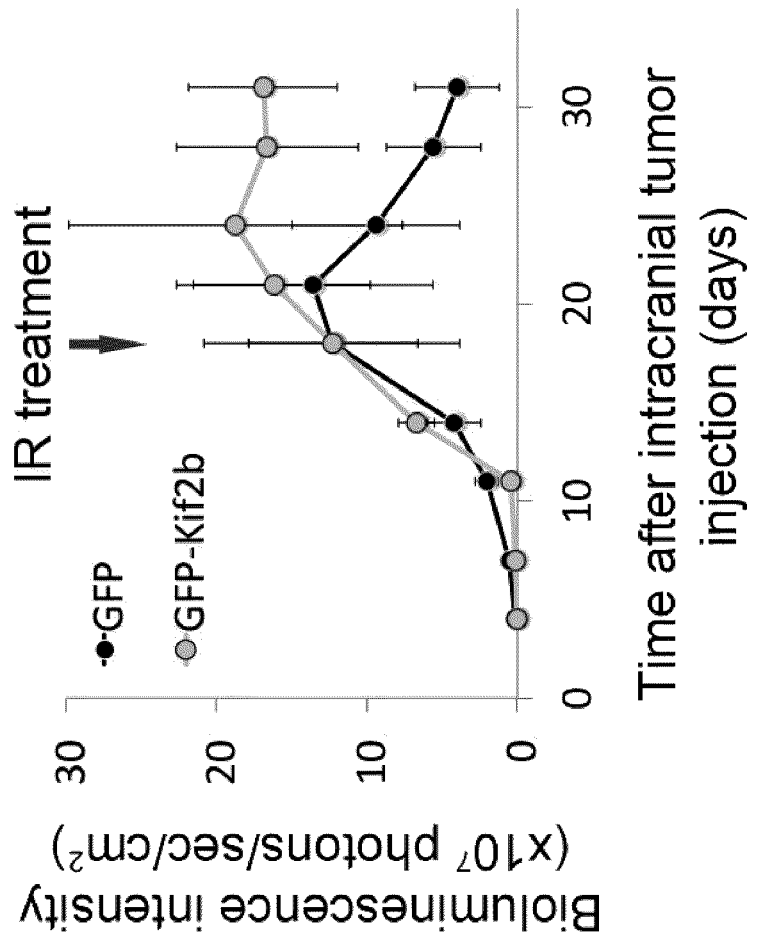
FIG. 9 is a plot of absolute bioluminescence signal as a function of time after intracranial injection of U251 cells expressing GFP or GFP-Kif2b. Data derived from a sample experiment. IR treatment (24Gy total) was administered starting on day 18 with 4Gy fractions every other day. The experiment was performed with three animals in each arm and was replicated three times. The data shows that Kif2b overexpression leads to tumor radiation resistance. Error bars show the standard error of the mean (SEM) of animals within an arm of a representative experiment.

To test the relationship between chromosome segregation errors and tumour response to radiation in vivo, U251 cells expressing firefly luciferase and either GFP or GFP-Kif2b we intracranially transplanted into athymic mice. Eighteen days after cell injection, six fractions of 4 Gy (24 Gy total) were delivered over a period of 13 days (see experimental schema in FIG. 6A). This dose fractionation regimen aimed at targeting the most sensitive subpopulation of tumour cells—which include those undergoing mitosis during IR exposure—over multiple days while allowing cell cycle redistribution in the interval between radiation doses. Absolute bioluminescence values before the initiation of treatment increased at comparable rates in GFP- and GFP-Kif2b-overexpressing tumours suggesting similar tumour growth rates (FIG. 9). Tumours overexpressing only GFP showed a robust response to radiation treatment as judged by approximately tenfold reduction in luciferase signal at the end of the treatment course (FIGS. 6B-D). In contrast, there was striking resistance to radiation treatment in tumours derived from cells overexpressing GFP-Kif2b (FIGS. 6B-D). For example, FIG. 6C shows normalized bioluminescence of intracranial U251 xenografts overexpressing GFP or GFP-Kif2b after initiation of IR treatment. As shown in FIG. 6C, while cells expressing only GFP displayed significant response to IR 14 days following the treatment, U251 cells overexpressing GFP-Kif2b exhibited significant resistance to IR at same time points. In order to make sure that the observed results are not due to the proliferation differences between the U251 cells overexpressing GFP and GFP-Ki2fb, the inventors analyzed the levels of proliferation marker Ki67. As shown in FIGS. 6E and 6F, overexpression of Kif2b did not influence cellular proliferation. Moreover, U251 xenografts overexpressing GFP or GFP-Kif2b exhibited comparable mitotic indices (FIG. 6G).

GFP- and GFP-Kif2b-expressing tumours also exhibited similar frequencies of multipolar mitoses known to occur after radiation exposure (Sato et al. *Oncogene* 19, 5281-5290 (2000)), FIGS. 6H and 6I. However, GFP-Kif2b-expressing tumours displayed decreased apoptosis as indicated by lower cleaved caspase 3 staining (FIGS. 6J and 6K). Therefore, suppression of numerical chromosomal instability by altering kinetochore-microtubule attachment stability leads to significant radiation resistance likely by suppressing cell death resultant from excessive chromosomal damage.

Example 9

Prophetic

Testing Whether Pharmacologically Inducing CIN Sensitizes TNBC to Radiation Treatment Maximizing tumor response to radiation treatment represents an important clinical goal in regionally advanced or metastatic triple negative breast cancer (TNBC), respectively. In Example 8, the inventors have shown that suppressing chromosome missegregation rates leads to significant tumor radio-resistance in vivo, suggesting that the opposite act of increasing chromosome missegregation would lead to increase tumor susceptibility to DNA-damaging therapies.

To test whether increasing CIN sensitizes TNBC to radiation treatment, a genetically engineered mouse model will be used, which recapitulates genetic alterations in both BRCA1-related and sporadic TNBC, including loss of the tumor suppressors p53 and inpp4b with or without *brca1* (*Cancer Genome Atlas Network. Comprehensive molecular portraits of human breast tumours. Nature* 490, 61-70 (2012)). p53 and *brca1* were conditionally knocked-out through introduction of Cre-recombinase driven by the Cytokeratin 14 (K14)-promoter and these mice were mated with littermates heterozygous for inpp4b. Under this genetic background, ~58% of 60 mice developed spontaneous intra-ductal carcinomas characterized with high-grade pleomorphic nuclei, significant chromosome copy number alterations (CNAs) and numerous mitoses, highly resembling human TNBC. In addition to this genetically engineered mouse model, patient-derived xenograft model will be used as well. Briefly, $10^5$ cells will be transplanted in the mammary fat pads of immuno-competent BL6 hosts. Once tumors reach 5-mm in diameter, 2Gy daily fractions to a total dose of 24Gy or a biologically equivalent single-dose of 13Gy will be delivered using the JLShepherd @ Associates irradiator (model: MK1-68). Animals will then be treated with either placebo or CFI-400945, a small molecule inhibitor of Plk4, known to increase chromosome missegregation rates in breast cancer cell lines by inducing supernumerary centrosomes and lagging chromosome formation (Ganem et al. *Nature* 460, 278-282 (2009), Silkworth et al. *PLoS ONE* 4, e6564 (2009), Mason et al. *Cancer Cell* 26, 163-176 (2014)).

Interestingly, breast cancer cell lines are highly dependent on Plk4 function and loss of tumor suppressor phosphatase and tensin homolog (PTEN), a frequent occurrence in TNBC, is synthetically lethal with loss of Plk4 activity Brough, R. et al. *Cancer Discovery* 1, 260-273 (2011)), making the latter an attractive target to further explore in combination with established therapies in TNBC.

CFI-400945 will be administered at a concentration of 9.4 mg/kg daily for 2 weeks as previously described (Mason et al. *Cancer Cell* 26, 163-176 (2014)). Tumor response will be measured using calipers and bioluminescence imaging. Additionally, measures of the time-to-relapse will be taken and direct comparison will be made between BRCA-proficient and BRCA-deficient tumors. For statistical methods please see Vertebrate Animals section. Targeted sequencing and FISH will be to used assess the PTEN status of these tumors given the known synthetic lethality with the loss of PTEN and plk4.

Example 10

A Computational Model of CIN in Clonally Expanding Populations

Ability to quantitatively study the dynamics of drug resistance and tumor relapse hinges on our capacity to identify, track, and ideally predict the emergence of resistant tumor subclones. A significant challenge arises, however, which is to understand the collective behavior of tumor cells based on our knowledge of single-cell parameters. To address this and understand how CIN influences the evolution of clonal populations, the inventors developed an experimentally inspired stochastic model of tumor evolution using the Monte Carlo method and a Markov-chain model (Laughney et al. *Cell Rep* 12, 809-820 (2015)). This model is based on the potency and chromosomal distribution of oncogenes and tumor suppressor genes on individual chromosomes (Davoli, T. et al. *Cell* 155, 948-962 (2013)), whereby clonally expanding population were able to sample the aneuploid fitness landscape as they continuously underwent chromosome missegregation. Cellular viability was determined by the chromosomal content such that more copies of oncogenic chromosomes led to a higher probability of continued division (FIG. 11A). Tumor viability was then assessed as a function of chromosome missegregation. Tumor viability was assessed by either measuring 1) clonal fitness that was defined as the product of phenotypic heterogeneity and clonal survival or 2) adaptive capacity, which measured how rapidly a clonal population was able to mobilize across the aneuploid fitness landscape from a low fitness state to a higher fitness state. Using these two orthogonal approaches, the inventors found that the viability of tumor cell populations was maximized at a chromosome missegregation frequency of $1.9 \times 10^{-3}$ per chromosome copy per cell division (FIGS. 11B-C). Strikingly, when four chromosomally unstable cell lines derived from human breast, bone, and colorectal cancers were experimentally assayed, it was found that their chromosome missegregation rates fell at or very close to this optimal missegregation frequency (FIG. 11B). This implies the presence of an evolutionary pressure on chromosome missegregation rates that balance clonal survival with cellular viability and allows clonal populations to rapidly acquire fitter karyotypes. It also provides insight into why CIN may represent a predictive marker of response to therapies that are known to induce chromosome missegregation (Jamal-Hanjani, M. et al. *Annals of Oncology* 26, 1340-1346 (2015), Zaki, et al. *Cancer* 120, 1733-1742 (2014)); these therapies likely drive a tumor from an optimal fitness state to a state so chromosomally unstable that it is no longer compatible with viability.

Results by Laughney et al. support the findings disclosed in the present disclosure, as they corroborate that cancer cells can tolerate certain level of chromosomal segregation errors beyond which they exhibit a "meltdown". Moreover, the authors provide optimal chromosome missegregation frequency ($1.9 \times 10^{-3}$) per chromosome copy per cell division, at which viability of tumor cell populations is maximized.

The present inventors have discovered that increasing chromosome missegregation together with radiation treatment would lead to sensitization of the tumor to radiation therapy. This in turn permits 1) to decrease dose of radiation and achieve the same effect, 2) to maintain dose of radiation and increase tumor sensitization in otherwise resistant tumors, 3) to increase radioprotection of normal organs.

The materials methods and measurements and the particular Examples described herein are not limiting and the same assessments and practices of the methods described herein can be made using alternative techniques known in the art. All cited references are incorporated by reference in their entirety.

What is claimed is:

1. A method for increasing susceptibility of cancer cells to ionizing radiation comprising:
exposing the cancer cells to an effective amount of a radiosensitizing agent, which specifically perturbs the process of chromosome segregation, inducing misaggregation, or specifically inhibits a second agent that promotes faithful chromosome segregation, the radiosensitizing agent thereby inducing numeric chromosome instability in the cells simultaneously with or closely prior to or closely after irradiating the cells with a therapeutically effective dose and regimen of ionizing radiation,
wherein the radiosensitizing agent is selected from the group consisting of Kif2b inhibitors, MCAK inhibitors, Eg5/Kinesin-5 inhibitors, Polo-like kinase 4 inhibitors, NORAD inhibitors, MAD2 inhibitors, and Hec1 inhibitors.

2. The method of claim 1 wherein the radiosensitizing agent specifically inhibits one or more of Kif2b, MCAK, Eg5/Kinesis-5, Polo-like kinase 4, NORAD, MAD2, and Hec1.

3. The method of claim 1 wherein the cancer cells are solid tumor cancer cells.

4. The method of claim 1 wherein the ionizing radiation is administered in two or more divided doses.

5. The method of claim 1, wherein the radiosensitizing agent is a Kif2b inhibitor.

6. The method of claim 1, wherein the radiosensitizing agent is a MCAK inhibitor.

* * * * *